United States Patent [19]

Hirasawa et al.

[11] Patent Number: 5,229,400
[45] Date of Patent: Jul. 20, 1993

[54] PIPERIDINE COMPOUNDS AND THEIR USE AS ANTIARRHYTHMIC AGENTS

[75] Inventors: Akira Hirasawa; Masataka Shoji; Ryota Yoshimoto; Yuichi Gyotoku; Chikahiko Eguchi, all of Kawasaki, Japan

[73] Assignee: Ajinomoto Co., Inc., Tokyo, Japan

[21] Appl. No.: 770,892

[22] Filed: Oct. 4, 1991

[30] Foreign Application Priority Data

Oct. 5, 1990 [JP] Japan ................ 2-269193

[51] Int. Cl.$^5$ ............... A61K 31/445; C07D 211/70
[52] U.S. Cl. ..................... 514/325; 546/203
[58] Field of Search .............. 514/325; 546/203

[56] References Cited

FOREIGN PATENT DOCUMENTS 0180810 5/1986 European Pat. Off.
0294183 12/1988 European Pat. Off.
0370712 5/1990 European Pat. Off.
0371805 6/1990 European Pat. Off. ............ 546/203

OTHER PUBLICATIONS

Chemical Abstracts, vol. 106, No. 25, Jun. 22, 1987, p. 645, No. 213767z, H. Sugimoto, et al.,
Hackh Chemical Dictionary, 1969, p. 160.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

A piperidine derivative of general formula (I) or a pharmaceutically acceptable salt thereof:

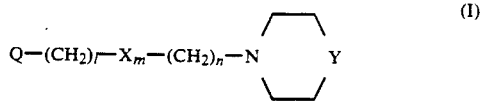

wherein

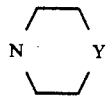

is any of several specified aromatic-containing groups; X is selected from one of several hetero atom-containing groups or $C_2$ alkylene or a cyano-containing group; and Q is phenyl, cyclohexyl, piperidinyl, tetrahydropyranyl, pyridyl, pyrrolyl, N-methylpyrrolyl, thienyl, furyl, 1-hexyl, or cyano; from 1 to 3 hydrogen atoms in Q may be independently substituted by alkyl of from 1 to 3 carbon atoms, perfluoroalkyl of from 1 to 3 carbon atoms, acylamino of from 1 to 6 carbon atoms, perfluoroacylamino of from 1 to 3 carbon atoms, alkoxy of from 1 to 3 carbon atoms, alkanesulfonylamino of from 1 to 3 carbon atoms, perfluoroalkanesulfonylamino of from 1 to 3 carbon atoms, acetoxy of from 1 to 3 carbon atoms, aminocarbonyl, aminosulfonyl, fluoro, chloro, cyano, hydroxy, nitro, amino, imidazolylmethyl, cinnamoylamino, p-fluorobenzoyl, cyanomethyl, cyanoethyl, methoxyacetoxy, alkoxycarbonyl of from 1 to 3 carbon atoms; l is an integer of from 0 to 1; m is an integer of from 0 to 1; n is an integer of from 0 to 6.

The derivatives are useful as antiarrhythmic agents.

5 Claims, No Drawings

PIPERIDINE COMPOUNDS AND THEIR USE AS ANTIARRHYTHMIC AGENTS

FIELD OF THE INVENTION

The present invention relates to novel antiarrhythmic agents, more particularly to novel piperidine derivatives and their use in the treatment of arrhythmia.

BACKGROUND OF THE INVENTION

Arrhythmia is the disfunction of cardiac normal conduction, which is a life-threatening disease, because it disturbs the rhythmic beating of the heart, worsening hemodynamics. Therefore, therapy for cardiac arrhythmia is clinically essential.

Antiarrhythmic drugs have been grouped together according to the pattern of mechanism: Na channel blocker, Beta blocker, Ca channel blocker and drugs which prolong Repolarization. Drug therapy of cardiac arrhythmias is not established, because many drugs have severe adverse effects, such as undesirable hemodynamic effects, hypotension, gastrointestinal symptoms, effects on the central nervous system and arrhythmogenic effects. Also, at higher plasma concentrations of drug, cardiac toxicity may become severe, so the monitoring of plasma concentration is essential for drug therapy.

It is therefore required to develop new antiarrhythmic drugs having excellent pharmaceutical effects and safety which can be industrially prepared at low cost in a simple manner.

DISCLOSURE OF THE INVENTION

It has now been found that certain piperidine derivatives have antiarrhythmic activity, which derivatives are represented by the following general fomula (I):

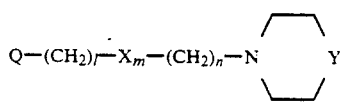

wherein

is any of the following groups:

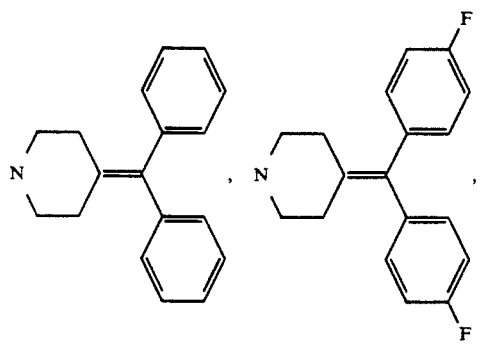

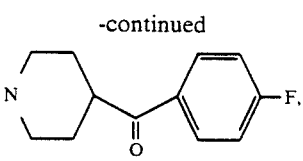

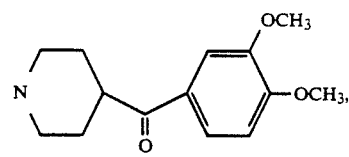

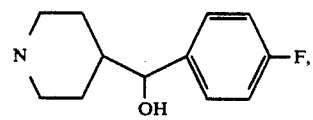

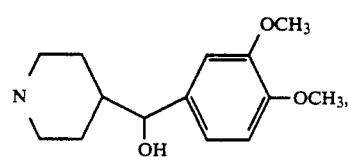

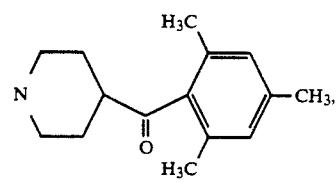

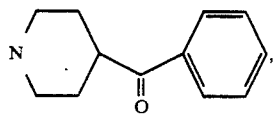

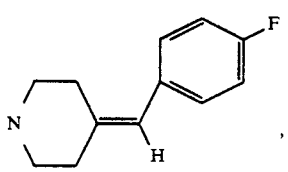

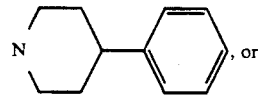

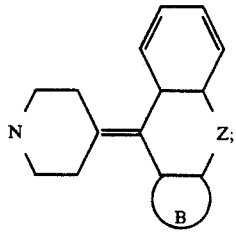

wherein B is a fused aromatic or heterocyclic ring selected from the group consisting of benzene, pyridine and thiophene;

—Z— is selected from:

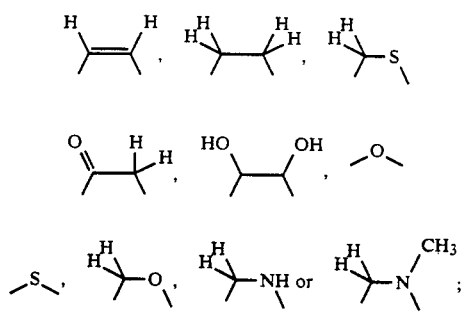

X is selected from:

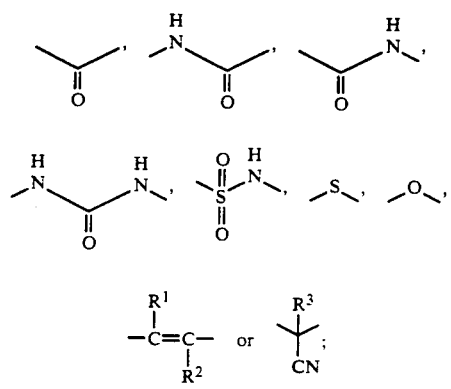

wherein $R^1$ and $R^2$ are the same or different and are independently selected from hydrogen, methyl, ethyl, or propyl; $R^3$ is hydrogen, alkyl of from 1 to 12 carbon atoms, or aryl of from 6 to 12 carbon atoms;

Q is phenyl, cyclohexyl, piperidinyl, tetrahydropyranyl, pyridyl, pyrrolyl, N-methylpyrrolyl, thienyl furyl, 1-hexyl, or cyano; from 1 to 3 hydrogen atoms in Q may be independently substituted by alkyl of from 1 to 3 carbon atoms, perfluoroalkyl of from 1 to 3 carbon atoms, acylamino of from 1 to 6 carbon atoms. perfluoroacylamino of from 1 to 3 carbon atoms, alkoxy of from 1 to 3 carbon atoms, alkanesulfonylamino of from 1 to 3 carbon atoms, perfluoroalkanesulfonylamino of from 1 to 3 carbon atoms, acetoxy of from 1 to 3 carbon atoms, aminocarbonyl, aminosulfonyl, fluoro, chloro, cyano, hydroxy, nitro, amino, imidazolylmethyl, cinnamoylamino, p-fluorobenzoyl, cyanomethyl, cyanoethyl, methoxyacetoxy, alkoxycarbonyl of from 1 to 3 carbon atoms; l is an integer of from 0 to 1; m is an integer of from 0 to 1; n is an integer of from 0 to 6.

These compounds may be in their free base form or in the form of a pharmaceutically acceptable salt thereof.

A compound of the above formula can be prepared by the following procedure:

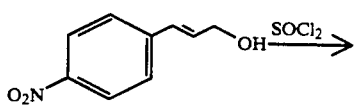

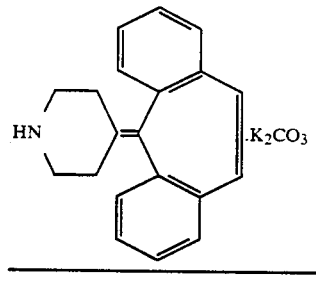

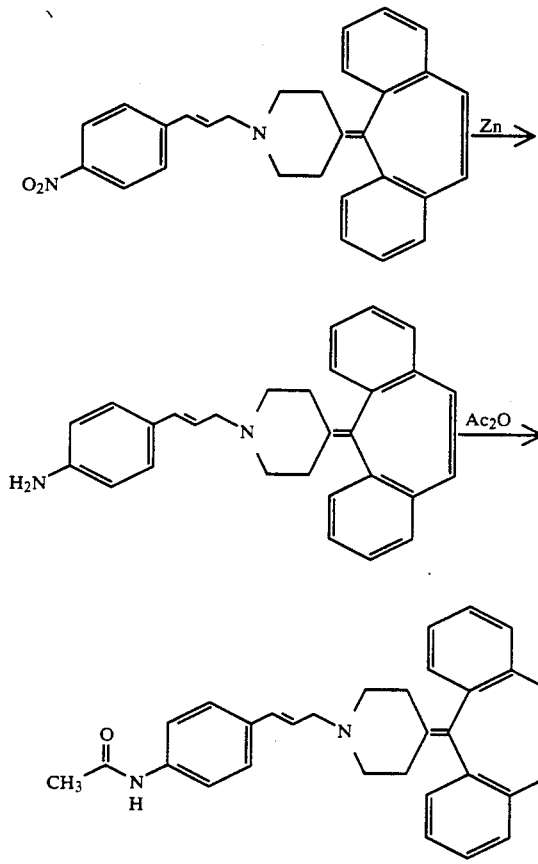

The pharmaceutically acceptable salts of the piperidine derivatives of this invention are acid addition salts formed from the compound and an organic or inorganic acid well known in the art as providing a pharmaceutical addition salt, such as a hydrochloride, sulfate, citrate, tartarate, mesylate, maleate, fumarate, or the like.

These salts are readily prepared by mixing a solution of equimolar amounts of the free base form of the compound and desired acid in a suitable solvent such as water, alcohol, or ether, followed by recovery of the product by collecting the precipitated salt or by evaporation of the solvent.

When used as antiarrhythmic drugs, the piperidine derivatives of the present invention may be administered by an oral or parenteral route, which may be determined depending upon age, body weight, condition of the patient. A daily dose may generally be from about 0.001 about 2000 mg/patient or animal for oral administration; in the case of patenteral administration, a daily dose may generally be from about 0.001 to about 1000 mg/patient or animal.

The piperidine derivatives of the present invention may be formulated into conventional preparation forms, for example, tablets, powders, capsules, solutions, sugar-coated tablets or depots, which may be prepared in a conventional manner using conventional techniques. For example, tablets can be obtained by mixing a piperidine derivative of the present invention with known auxiliary substances, for example, inactive diluents (e.g. lactose, calcium carbonate or calcium phosphate), binders (e.g. gum arabic, corn starch or gelatin), sweeteners (e.g. sucrose or saccharine), flavours (e.g. peppermint, Gaultheria adenothrix oil or cherry), lubricating and wetting agents (e.g. magnesium stearate, talc or carboxymethyl cellulose).

The present invention further provides a novel antiarrhythmic agent which is a composition comprising a pharmaceutically effective amount of a piperidine derivative as defined above.

The pharmaceutical composition of the present invention is advantageous as an antiarrhythmic drug for treating mammals including humans. This can be administered perorally in the form of tablet, capsule or elixir, or parenterally in the form of a sterile solution or suspension, for the purpose of reducing or eliminating arrhythmia. The pharmaceutical composition of the present invention can be administered to patients or animals which are to be treated generally several times each in a unit dosage of from about 0.001 to about 500 mg/patient or animal, and accordingly the total dosage of the derivative may be from about 0.001 to about 2000 mg/patient or animal/day. Of course, the amount of the dosage may be varied in accordance with the condition of the disease, the weight of the patient or animal and other factors which are considered appropriate by one skilled in the art.

The above-mentioned typical combinations may be formulated as a pharmaceutical composition in a conventional manner. For example, from about 0.2 to about 500 mg of the derivative of the present invention or a pharmaceutically acceptable salt thereof or a mixture thereof is blended together with a pharmaceutically acceptable vehicle, carrier, extender, binder, antiseptic, stabilizer, flavour and the like, in an amount as required for conventional pharmaceutical preparations.

Examples of pharmaceutical additives to be used for the preparation of tablets, capsules and the like are: binders such as tragacanth, gum arabic, corn starch or gelatin; vehicles such as fine crystalline cellulose; extenders such as corn starch, pre-gelatinised starch or alginic acid; sweeteners such as sucrose, lactose or saccharin; flavours such as peppermint, an oil from Gaulthenia adenothrix Maxim or cherry. When the preparation is in the form of a capsule, this may further contain a liquid carrier such as a fat and oil, in additional to the above mentioned materails. Other various materails can further be employed so as to form coated pills or to vary the physical form of the preparation by a different method. For example, tablets can be coated with shellac, sugar or both. A syrup or elixir can contain the active compound together with sucrose as a sweetener, methyl- or propyl-paraben as an antiseptic, a dye, and cherry or orange essence as a flavour.

A sterile composition for injection can be prepared in a conventional manner, for example, by dissolving or suspending the active substance in a vehicle such as distilled water for injection, together with a natural vegetable oil such as sesame oil, coconut oil, peanut oil, cotton seed oil, or a synthetic fat vehicle such as ethyl oleate. If desired, a buffer, an antiseptic, an antioxidant or the like can be incorporated into the composition.

The present invention will be further illustrated by reference to the following examples.

PREPARATION OF COMPOUNDS

Retention factor (Rf) was determined by silica gel thin layer chromatography (TLC:Merck Art 5715). Unless otherwise noted, mass spectroscopy was determined on JEOL-DX 300 by FD mode; $^1$H NMR spectra were obtain in $CDCl_3$ with tetramethylsilane as internal standard on a Varian VXR-300 spectrometer. "Intermediate (1)" represents 4-(5H-dibenzo[a, d]cyclohepten-5-ylidene)piperidine.

COMPOUND 1

4-(5H-Dibenzo[a,d]cyclohepten-5-ylidene)-1-[4-(N-imidazolylmethyl)cinnamyl]piperidine To a solution of 4-(N-imidazolylmethyl)cinnamic alcohol (4.5 mmol) in CHCl3, thionyl chloride (5.4 mmol) was added, and stirred for 2 h at room temperature. After a usual procedure, the product was used without further purification.

The product obtained according to above-mentioned procedure was dissolved in methyl isobutyl ketone, and then intermediate (1) (4.0 mmol), potassium carbonate (8.75 mmol) and NaI (8.75 mmol) were added to the solution, stirred at 90° C. for overnight. The mixture was washed with water, extracted with CH2Cl2, washed with 1M HCl, saturated aqueous solution of NaHCO3, and then brine, dried over MgSO4. The solvent was evaporated at reduced pressure, the resulting mixture was purified by column chromatography (SiO2).

| MS | 469(M+) |
|---|---|
| NMR | |
| 2.2–2.4(4H, m) | 2.5–2.6(2H, m) |
| 2.8–2.9(2H, m) | 3.28(2H, d) |
| 5.07(2H, s) | 6.38(1H, dt) |
| 6.52(1H, d) | 6.95(2H, s) |
| 7.0–7.6(15H, m) | |

COMPOUND 2

1-[4-[4-(5H-Dibenzo[a,d]cyclohepten-5-ylidene)-1-piperidinyl]butanoyl]-1-hydroxypiperidine

| TLC(CHCl3:MeOH=9:1) | Rf=0.58 |
|---|---|
| MS | 442(M+) |
| NMR | |
| 1.4–1.6(2H, m) | 1.8–2.0(4H, m) |
| 2.1–2.2(4H, m) | 2.3–2.4(4H, m) |
| 2.5–2.6(2H, m) | 2.89(1H, m) |
| 3.19(1H, m) | 3.7–3.8(2H, m) |
| 3.9–4.0(2H, m) | 4.0–4.2(2H, m) |
| 6.91(2H, s) | 7.1–7.4(8H, m) |

COMPOUND 3

4-[4-Dibenzo[b,e]thiepin-11(6H)-ylidene]-1-piperidinyl]-1-cyclohexylbutane

According to the practically same procedure described in preparation of compound 1,4-bromo-1-cyclohexylbutane and 4-dibenzo[b,e]thiepine-11-(6H)-ylidenepiperidine were used.

| | |
|---|---|
| TLC(CHCl3:MeOH=9:1) | Rf=0.74 |
| MS | 431(M+) |
| NMR | |
| 0.8–1.0(2H, m) | 1.1–1.4(10H, m) |
| 1.4–1.6(1H, m) | 1.6–1.8(6H, m) |
| 2.1–2.4(4H, m) | 2.51(2H, t) |
| 2.6–2.8(4H, m) | 3.39(1H, d) |
| 4.99(1H, s) | 6.9–7.1(4H, m) |
| 7.2–7.4(4H, m) | |

COMPOUND 4

4-(5H-Dibenzo[a,d]cyclohepten-5-ylidene)-1-(4-nitrocinnamyl)piperidine

After the stepwise addition of 4-Nitrocinnamyl alcohol (5.58 mmol) to a ice-cooled solution of SOCl2 (10 g), the mixture was stirred for a few minites. The residue obtained by general procedure was condensed with intermediate (1) (6.59 mmol) in the presence of potassium carbonate. Yield 2.02 mmol (36.2%)

| | |
|---|---|
| MS | 434(M+) |
| NMR | |
| 2.16–2.24(4H, m) | 2.31–2.42(2H, m) |
| 2.60–2.68(2H, m) | 3.18(2H, d) |
| 6.46(1H, dt) | 6.55(1H, d) |
| 6.92(2H, s) | 7.18–7.36(8H, m) |
| 7.42–7.48(2H, m) | 8.17–8.20(2H, m) |

COMPOUND 5

1-(4-Aminocinnamyl)-4-(5H-dibenzo[a,d]cyclohepten-5-ylidene)piperidine 4-(5H-Dibenzo[a,d]cyclohepten-5-ylidene)-1-(4-nitrocinnamyl)piperidine (compound 4) was reduced by zinc in acetic acid at room temperature for 4 h. Yield 84.5%

| | |
|---|---|
| MS | 404(M+) |
| NMR | |
| 2.20–2.42(6H, m) | 2.60–3.32(4H, m) |
| 3.40(2H, d) | 6.11(1H, dt) |
| 6.43(1H, d) | 6.59–6.64(2H, s) |
| 6.91(2H, s) | 7.14–7.36(10H, m) |

COMPOUND 6

1-(4-Acetylaminocinnamyl)-4-(5H-dibenzo[a,d]cyclohepten-5-ylidene)piperidine 1-(4-Aminocinnamyl)-4-(5H-dibenzo[a,d]cyclohepten-5-ylidene)piperidine (compound 5) was N-acetylated by acetic anhydride using triethyl amine as base. Yield 92.3%

| | |
|---|---|
| MS | 446(M+) |
| NMR | |
| 2.18(3H, s) | 2.20–2.55(6H, m) |
| 4.70(1H, bs) | 6.20(1H, dt) |
| 6.42(1H, d) | 6.91(2H, s) |
| 7.15–7.36(10H, m) | 7.42–7.56(2H, m) |

COMPOUND 7

3-[4-(5H-Dibenzo[a,d]-cyclohepten-5-ylidene)-1-piperidinyl]-1-(4-nitrophenyl)propane a) 1-Bromo-3-(4-nitrophenyl)propane 1-Bromo-3-phenylpropane (19.7 mmol) was added slowly to a solution of sulfuric acid (7.4 g) and nitric acid (5.4 g) at ambient temperature and stirred at 60° C. The residue (mixture of ortho and para) was purified by column chromatography on silica gel. Yield 63.7%

| | |
|---|---|
| NMR | |
| 2.20(2H, quint.) | 2.92(2H, t) |
| 3.40(2H, t) | 7.35(2H, d) |
| 8.16(2H, d) | | b) compound 7

This was prepared from 1-Bromo-3-(4-nitrophenyl)propane and intermediate (1). Yield 94.6%

| | |
|---|---|
| MS | 436(M+) |
| NMR | |
| 1.84(2H, m) | 2.15(4H, m) |
| 2.30(4H, m) | 2.59(2H, m) |
| 2.70(2H, t) | 6.90(2H, s) |
| 7.2–7.4(10H, m) | 8.10(2H, d) |

COMPOUND 8

1-(4-Aminophenyl)-3-[4-(5H-dibenzo[a,d]cyclohepten-5-ylidene)-1-piperidinyl]propane 3-[4-(5H-Dibenzo[a,d]cyclohepten-5-ylidene)-1-piperidinyl]-1-(4-nitrophenyl)propane (compound 7) was reduced by zinc. Yield 97.3%.

| | |
|---|---|
| MS | 406(M+) |
| NMR | |
| 1.70(2H, m) | 2.0–2.6(12H, m) |
| 3.48(2H, br) | 6.55(2H, d) |
| 6.85(2H, s) | 6.92(2H, d) |
| 7.20(4H, m) | 7.25(4H, m) |

COMPOUND 9

1-(4-Acetylaminophenyl)-3-[4-(5H-dibenzo[a,d]cyclohepten-5-ylidene)-1-piperidinyl]propane This was prepared from 1-(4-Aminophenyl)-3-[4-(5H-dibenzo[a,d]cyclohepten-5-ylidene)-1-piperidinyl]propane (compound 8) and acetic anhydride. Yield 92.9%

| | |
|---|---|
| MS | 48(M+) |
| NMR | |
| 1.6–1.8(4H, m) | 2.15(3H, s) |
| 2.0–2.2(2H, m) | 2.2–2.4(4H, m) |
| 2.55(4H, m) | 7.1–7.4(12H, m) |

COMPOUND 10

N-[3-(5H-Dibenzo[a,d]cyclohepten-5-ylidene)-1-piperidinyl]propanoyl-3,4-dimethoxyanilide

| | |
|---|---|
| MS(FAB, m/z) | 481(M+) |
| NMR | |
| 2.25–2.36(4H, m) | 2.40–2.46(2H, m) |
| 2.52(2H, t) | 2.70(2H, t) |
| 2.68–2.80(2H, m) | 3.85(3H, s) |
| 3.88(3H, s) | 6.79(2H, s) |
| 6.93(2H, s) | 7.18–7.35(8H, m) |
| 7.52(1H, s) | |

COMPOUND 11

4-[4-[4-(5H-Dibenzo[a,d]cyclohepten-5-ylidene)-1-piperidinyl]-1-butyl]tetrahydropyran

| MS | 413(M+) |
|---|---|
| NMR | |
| 1.1–1.6(10H, m) | 1.7–1.8(1H, m) |
| 2.1–2.4(8H, m) | 2.5–2.6(2H, m) |
| 3.35(2H, t) | 3.93(2H, d) |
| 6.90(2H, s) | 7.2–7.4(8H, m) |

COMPOUND 12

1-(N-Acetyl-4-piperidinyl)-3-[4-(5H-dibenzo[a,d]cyclohepten-5-ylidene)-1-piperidinyl]propane a) 3-(4-Piperidinyl)-1-propanol 1-(4-Pyridyl)-1-propine-3-ol was hydrogenated with rhodium on alumina as catalyst.

b) 1-Acetoxy-3-(N-acetyl-4-piperidinyl)propane

This was prepared from 3-(4-Piperidinyl)-1-propanol and acetic anhydride.

| NMR | |
|---|---|
| 1.0–1.8(9H, m) | 2.04(3H, s) |
| 2.07(3H, s) | 2.51(1H, t) |
| 3.00(1H, t) | 3.78(1H, br d) |
| 4.04(2H, t) | 4.58(1H, br d) | c) 3-(N-Acetyl-4-piperidinyl)propanol

1-Acetoxy-3-(N-acetyl-4-piperidinyl)propane was saponificated by potassium carbonate.

| NMR | |
|---|---|
| 1.0–1.2(2H, m) | 1.2–1.4(2H, m) |
| 1.4–1.8(6H, m) | 2.08(3H, s) |
| 2.53(1H, dt) | 3.02(1H, dt) |
| 3.64(2H, t) | 3.79(1H, br d) |
| 4.58(1H, br d) | | d) 1-(N-Acetyl-4-piperidinyl)-3-bromopropane 3-(N-Aceytl-4-piperdinyl)propanol was brominated with phosphorus tribromide.

| NMR | |
|---|---|
| 1.0–1.2(2H, m) | 1.40(2H, t) |
| 1.50(1H, m) | 1.74(2H, br t) |
| 1.78(2H, quint) | 2.08(3H, s) |
| 2.53(1H, dt) | 3.02(1H, dt) |
| 3.40(2H, t) | 3.80(1H, br d) |
| 4.59(1H, br d) | | e) compound 12 Yield 77.8%

| MS | 440(M+) |
|---|---|
| NMR | |
| 1.0–1.2(2H, m) | 1.22(2H, m) |
| 1.4–1.6(3H, m) | 1.68(2H, m) |
| 2.05(3H, s) | 2.1–2.6(11H, m) |
| 2.96(1H, dt) | 3.74(1H, br d) |
| 4.55(1H, br d) | 6.90(2H, s) |
| 7.2–7.4(8H, m) | |

COMPOUND 13

5-Acetylamino-2-[4-(5H-dibenzo[a,d]cyclohepten-5-ylidene)-1-piperidinyl]methylindan

| MS | 460(M+) |
|---|---|
| NMR | |
| 2.0–2.3(7H, m) | 2.3–2.5(1H, m) |
| 2.5–2.8(6H, m) | 2.9–3.1(2H, m) |
| 6.92(2H, s) | 7.0–7.5(11H, m) |

COMPOUND 14

4-(5H-Dibenzo[a,d]cyclohepten-5-ylidene)-1-(2,4-dimethoxycinnamyl)piperidine a) 4-(5H-Dibenzo[a,d]cyclohepten-5-ylidene)-1-(2,4-dimethoxycinnamoyl)piperidine 2,4-Dimethoxycinnamic acid (10.0 mmol) and intermediate (1) was condensed by N-ethyl-N'-(3-dimethylaminopropyl)carbodiimide hydrochloride.

b) compound 14

4-(5H-Dibenzo[a,d]cyclohepten-5-ylidene)-1-(2,4-dimethoxycinnamoyl)piperidine was reduced with lithium alminium hydride. Yield 12.3%

| MS | 449(M+) |
|---|---|
| NMR | |
| 2.13–2.23(4H, m) | 2.30–2.50(2H, m) |
| 2.62(2H, m) | 3.13(2H, d) |
| 3.78(6H, s) | 6.15(1H, tt) |
| 6.42(2H, m) | 6.68(1H, d, J=15.9Hz) |
| 6.91(2H, s) | 7.18–7.35(9H, m) |

COMPOUND 15

1-(4-Cyanocinnamyl)-4-(5H-dibenzo[a,d]cyclohepten-5-ylidene)piperidine a) 4-Cyanocinnamylalcohol A Heck reaction of 4-bromobenzonitrile and acrylic acid gave 4-cyanocinnamic acid. The acid was reduced to the corresponding alcohol with ethyl chloroformate and then sodium borohydride. Yield 78.6%

| NMR | |
|---|---|
| 4.38(2H, dd) | 6.49(1H, m) |
| 6.65(1H, d) | 7.44(2H, d) |
| 7.40(2H, d) | | b) compound 15

| MS | 414(M+) |
|---|---|
| NMR | |
| 2.12–2.22(4H, m) | 2.30–2.42(2H, m) |
| 2.52(2H, m) | 3.15(2H, d) |
| 6.42(2H, m) | 6.92(2H, s) |
| 7.18–7.35(8H, m) | 7.40(2H, d) |
| 7.58(2H, d) | |

COMPOUND 16

1-Cyclohexyl-4-[4-(10,11-dihydroxy-5H-dibenzo[a,d]cyclohepten-5-ylidene)-1-piperidinyl]butane A osmium tetraoxide (0.4 mmol) in acetone was added to the 50% aqueous solution of acetone dissolved in 1-Cyclohexyl-4-[4-(5H-dibenzo[a,d]cyclohepten-5-ylidene)-1-piperidinyl)butane (4.8 mmol) and N-methylmorpholine-N-oxide (7.2 mmol). The mixture was stirred for over night at ambient temperature.

| MS | 445(M+) |
|---|---|
| 0.7–1.4(11H, m) | 1.4–1.8(8H, m) |
| 2.6–3.0(8H, m) | 3.05(1H, bs) |
| 3.26(1H, bs) | 5.21(2H, s) |
| 7.0–7.6(4H, m) | |

COMPOUND 17

4-(5H-Dibenzo[a,d]cyclohepten-5-ylidene)-1-(4-propanoylaminocinnamyl)piperidine 1-(4-Aminocinnamyl)-4-(5H-dibenzo[a,d]cyclohepten-5-ylidene)piperidine (compound 5) was N-acylated. Yield 43.9%

| MS | 460(M+) |
|---|---|
| NMR | |
| 1.22(3H, t) | 2.2–2.6(8H, m) |
| 2.7–2.9(2H, m) | 3.23(2H, d) |
| 4.79(1H, bs) | 6.1–6.3(1H, m) |
| 6.43(1H, dd) | 6.93(2H, s) |
| 7.1–7.55(12H, m) | |

COMPOUND 18

4-(5H-Dibenzo[a,d]cyclohepten-5-ylidene)-1-(4-ethoxycarbonylaminocinnamyl)piperidine This compound was prepared from 1-(4-Aminocinnamyl)-4-(5H-dibenzo[a,d]cyclohepten-5-ylidene)-piperidine (compound 5) and ethyl chloroformate. Yield 56.7%

| MS | 476(M+) |
|---|---|
| NMR | |
| 1.30(3H, t) | 2.2–2.9(8H, m) |
| 3.26(2H, dd) | 4.22(2H, q) |
| 6.1–6.3(1H, m) | 6.46(1H, d) |
| 6.67(1H, bs) | 6.93(2H, s) |
| 7.1–7.4(12H, m) | |

COMPOUND 19

4-(5H-Dibenzo[a,d]cyclohepten-5-ylidene)-1-(4-methanesulfonylaminocinnamyl)piperidine This compound was prepared from 1-(4-Aminocinnamyl)-4-(5H-dibenzo[a,d]cyclohepten-5-ylidene)-piperidine (compound 5) and methanesulfonyl chloride. Yield 67.0%

| MS | 482(M+) |
|---|---|
| NMR | |
| 2.1–2.5(6H, m) | 2.5–2.7(2H, m) |
| 3.17(2H, d) | 3.39(3H, s) |
| 6.2–6.4(1H, m) | 6.49(1H, d) |
| 6.93(2H, s) | 7.1–7.5(12H, m) |

COMPOUND 20

4-(5H-Dibenzo[a,d]cyclohepten-5-ylidene)-1-(3-methoxycarbonylcinnamyl)piperidine According to the practical same procedure of compound 16, this compound was obtained.

| MS | 447(M+) |
|---|---|
| NMR | |
| 2.16–2.26(4H, m) | 2.30–2.44(2H, m) |
| 2.52(2H, m) | 3.14(2H, d) |
| 3.91(3H, s) | 6.38(1H, m) |
| 6.52(1H, d) | 6.92(2H, s) |
| 7.18–7.35(9H, m) | 7.52(1H, d) |
| 7.88(1H, d) | 8.01(1H, s) |

COMPOUND 21

4-(5H-Dibenzo[a,d]cyclohepten-5-ylidene)-1-(4-methoxycarbonylaminocinnamyl)piperidine This compound was prepared from 1-(4-Aminocinnamyl)-4-(5H-dibenzo[a,d]cyclohepten-5-ylidene)-piperidine (compound 5) and methyl chloroformate. Yield 97.5%

| MS | 462(M+) |
|---|---|
| NMR | |
| 2.2–2.9(8H, m) | 3.10(2H, m) |
| 3.78(3H, s) | 6.2–6.4(1H, m) |
| 6.56(1H, d) | 6.72(1H, bs) |
| 6.92(2H, s) | 7.1–7.4(12H, m) |

COMPOUND 22

4-(5H-Dibenzo[a,d]cyclohepten-5-ylidene)-1-(4-pivaloylaminocinnamyl)piperidine

This compound was prepared from 1-(4-Aminocinnamyl)-4-(5H-dibenzo[a,d]cyclohepten-5-ylidene)-piperidine (compound 5) and pivaloyl chloride. Yield 92.0%

| MS | 488(M+) |
|---|---|
| NMR | |
| 1.34(9H, s) | 2.2–3.2(10H, m) |
| 6.2–6.42(1H, m) | 6.55(1H, d) |
| 6.93(2H, s) | 7.1–7.44(10H, m) |
| 7.45–7.6(2H, m) | |

COMPOUND 23

4-(5H-Dibenzo[a,d]cyclohepten-5-ylidene)-1-(4-trifluoroacetylaminocinnamyl)piperidine This compound was prepared from 1-(4-Aminocinnamyl)-4-(5H-dibenzo[a,d]cyclohepten-5-ylidene)-piperidine (compound 5) and trifluoroacetic anhydride. Yield 46.0%

| MS | 500(M+) |
|---|---|
| NMR | |
| 2.4–3.7(10H, m) | 6.2–6.4(1H, m) |
| 6.58(1H, dd) | 6.93(2H, s) |
| 7.17(2H, d) | 7.2–7.45(8H, m) |
| 7.69(2H, dd) | 8.36(1H, bs) |

COMPOUND 24

1-(4-Butanoylaminocinnamyl)-4-(5H-dibenzo[a,d]cyclohepten-5-ylidene)piperidine

This compound was prepared from 1-(4-Aminocinnamyl)-4-(5H-dibenzo[a,d]cyclohepten-5-ylidene)-piperidine (compound 5) and butanoic acid. Yield 68.5%

| MS | 474(M+) |
|---|---|
| NMR | |
| 0.99(3H, q) | 1.6–1.8(2H, m) |
| 2.2–2.43(6H, m) | 2.44–2.7(2H, m) |
| 2.8–3.1(2H, m) | 3.35(2H, d) |
| 5.50(1H, bs) | 6.1–6.3(1H, m) |
| 6.45(1H, dd) | 6.92(2H, s) |
| 7.1–7.4(10H, m) | 7.49(2H, dd) |

The following compound were prepared according to the above-mentioned procedures.

COMPOUND 25

1-(4-ethoxycarbonylaminocinnamyl)-4-(4-fluorobenzoyl)piperidine

| MS | 410(M+) |
|---|---|
| NMR | |
| 1.33(3H, t) | 1.8–2.4(6H, m) |
| 3.18(2H, m) | 3.43(3H, m) |
| 4.21(2H, m) | 6.32(1H, dt) |
| 6.58(1H, d) | 6.6(1H, s) |
| 7.1–7.4(6H, m) | 7.92(2H, m) |

COMPOUND 26

4-(4-Fluorobenzoyl)-1-(4-methoxycarbonylaminocinnamyl)piperidine

| MS | 396(M+) |
|---|---|
| NMR | |
| 1.9–2.3(4H, m) | 2.70(3H, m) |
| 3.28(2H, m) | 3.42(3H, m) |
| 3.99(3H, m) | 6.33(1H, dt) |
| 6.58(1H, d) | 6.80(1H, s) |
| 7.1–7.5(6H, m) | 7.97(2H, m) |

COMPOUND 27

4-(4-Fluorobenzoyl)-1-(4-propanoylaminocinnamyl)piperidine

| MS | 394(M+) |
|---|---|
| NMR | |
| 1.23(3H, t) | 1.7–2.2(6H, m) |
| 2.41(2H, q) | 3.1–3.5(5H, m) |
| 6.33(1H, dt) | 6.58(1H, d) |
| 7.0–7.5(7H, m) | 7.98(2H, m) |

COMPOUND 28

4-(4-Fluorobenzoyl)-1-(4-trifluoroacetylaminocinnamyl)piperidine

| MS | 435(M+) |
|---|---|
| NMR | |
| 2.1–2.2(4H, m) | 2.95–3.3(5H, m) |
| 3.80(2H, m) | 6.25(1H, dt) |
| 6.68(1H, d) | 7.1–7.5(7H, m) |
| 7.98(2H, m) | |

COMPOUND 29

1-(4-Acetylaminocinnamyl)-4-(4-fluorobenzoyl)piperidine

| MS | 380(M+) |
|---|---|

-continued

| NMR | |
|---|---|
| 1.75–1.95(5H, m) | 2.1–2.3(4H, m) |
| 3.0–3.3(5H, m) | 6.22(1H, dt) |
| 6.50(1H, d) | 7.05–7.55(7H, m) |
| 7.98(2H, m) | |

COMPOUND 30

1-(4-Aminocinnamyl)-4-(4-fluorobenzoyl)piperidine

| MS | 338(M+) |
|---|---|
| NMR | |
| 1.8–2.2(4H, m) | 2.95–3.3(5H, m) |
| 3.68(2H, m) | 6.10(1H, dt) |
| 6.41(1H, d) | 6.62(2H, m) |
| 7.05–7.40(6H, m) | 7.97(2H, m) |

COMPOUND 31

4-(4-Fluorobenzoyl)-1-(4-nitrocinnamyl)piperidine

| MS | 368(M+) |
|---|---|
| NMR | |
| 1.8–2.2(4H, m) | 3.0–3.35(5H, m) |
| 3.8(2H, m) | 6.36(1H, dt) |
| 6.57(1H, d) | 7.05–7.5(6H, m) |
| 7.98(2H, m) | |

COMPOUND 32

1-(4-Aminocarbonylcinnamyl)-4-(5H-dibenzo[a,d]cyclohepten-5-ylidene)piperidine

| TLC(CHCl3:MeOH=9:1) | Rf=0.23 |
|---|---|
| MS | 432(M+) |

COMPOUND 33

4(5H-Dibenzo[a,d]cyclohepten-5-ylidene)-1-(4-trifluoromethylcinnamyl)piperidine

| TLC(CHCl3:MeOH=9:1) | Rf=0.85 |
|---|---|
| MS | 457(M+) |

COMPOUND 34

4-(5H-Dibenzo[a,d]cyclohepten-5-ylidene)-1-(4-cyanomethylcinnamyl)piperidine

| TLC(CHCl3:MeOH=9:1) | Rf=0.89 |
|---|---|
| MS | 428(M+) |

COMPOUND 35

4-(5H-Dibenzo[a,d]cyclohepten-5-ylidene)-1-(3,4-dichlorocinnamyl)piperidine

| TLC(CHCl3:MeOH=9:1) | Rf=0.72 |
|---|---|
| MS | 457(M+) |

COMPOUND 36

4-(5H-Dibenzo[a,d]cyclohepten-5-ylidene)-1-(3,4-dimethoxy-2-nitrocinnamyl)piperidine

| TLC(HEXANE:Ethyl acetate=1:1) | Rf=0.13 |
|---|---|
| MS | 457(M+) |

COMPOUND 27

4-Dibenzo[b,e]thiepin-11-(6H)-ylidene-1-(4-nitrocinnamyl)piperidine

| TLC(CHC13:MeOH=9:1) | Rf=0.89 |
|---|---|
| MS | 454(M+) |
| NMR | |
| 2.1–2.3(4H, m) | 2.4–2.6(2H, m) |
| 2.6–2.8(2H, m) | 3.21(2H, d) |
| 3.41(1H, d) | 4.98(1H, d) |
| 6.48(1H, dt) | 6.61(1H. d) |
| 7.0–7.1(4H, m) | 7.2–7.4(4H, m) |
| 7.4–7.5(2H, m) | 8.1–8.2(2H. m) |

COMPOUND 38

1-(4-Aminocinnamyl)-4-dibenzo[b,e]thiepin-11(6H)-ylidenepiperidine

| TLC(CHC13:MeOH=9:1) | Rf=0.65 |
|---|---|
| MS | 424(M+) |
| NMR | |
| 2.1–2.8(8H. m) | 3.13(2H, d) |
| 3.39(1H, d) | 3.68(2H, bs) |
| 4.95(1H, d) | 6.08(1H. dt) |
| 6.39(1H, d) | 6.5–6.6(2H, m) |
| 7.0–7.1(5H, m) | 7.1–7.3(5H. m) |

COMPOUND 39

1-(4-Acethylaminocinnamyl)-4-dibenzo[b,e]thiepin-11(6H)-ylidenepiperidine

| TLC(CHC13:MeOH=9:1) | Rf=0.58 |
|---|---|
| MS | 466(M+) |
| NMR | |
| 2.15(3H, s) | 2.2–2.9(8H, m) |
| 3.22(2H, d) | 3.40(1H, d) |
| 4.91(1H, d) | 6.21(1H, dt) |
| 6.48(1H, d) | 7.0–7.5(13H. m) |

COMPOUND 40

4-(5H-Dibenzo[a,d]-cyclohepten-5-ylidene)-1-(2,5-dimethoxycinnamyl)piperidine

| TLC(CHC13:MeOH=9:1) | Rf=0.73 |
|---|---|
| MS | 449(M+) |
| NMR | |
| 2.05–2.23(4H, m) | 2.30–2.45(2H, m) |
| 2.50–2.66(2H, m) | 3.15(2H, d) |
| 3.75(6H, s) | 6.15(1H, m) |
| 6.45–7.00(4H, m) | 6.91(2H, s) |
| 7.18–7.35(8H, m) | |

COMPOUND 41

4-(5H-Dibenzo[a,d]cyclohepten-5-ylidene)-1-(2,3-dimethoxycinnamyl)piperidine

| TLC(CHC13:MeOH=9:1) | Rf=0.90 |
|---|---|
| MS | 449(M+) |
| NMR | |
| 2.1–2.2(4H, m) | 2.3–2.4(2H, m) |
| 2.5–2.7(2H, m) | 3.13(2H, d) |
| 3.77(3H, s) | 3.80(3H, s) |
| 6.28(1H, dt) | 6.79(1H, d) |
| 6.90(2H, s) | 7.0–7.1(2H, m) |
| 7.2–7.4(9H. m) | |

COMPOUND 42

4-(5H-Dibenzo[a,d]cyclohepten-5-ylidene)-1-(3,5-dimethoxycinnamyl)piperidine

| TLC(CHC13:MeOH=9:1) | Rf=0.73 |
|---|---|
| MS | 449(M+) |
| NMR | |
| 2.05–2.23(4H, m) | 2.28–2.42(2H, m) |
| 2.50–2.66(2H, m) | 3.10(2H, d) |
| 3.78(6H, s) | 6.10–6.42(3H, m) |
| 6.52(2H. m) | 6.91(2H, s) |
| 7.18–7.35(8H, m) | |

COMPOUND 43

4-(5H-Dibenzo[a,d]cyclohepten-5-ylidene)-1-(2-methoxycinnamyl)piperidine

| TLC(CHC13:MeOH=9:1) | Rf=0.87 |
|---|---|
| MS | 419(M+) |
| NMR | |
| 2.2–2.3(4H, m) | 2.3–2.4(2H, m) |
| 2.6–2.7(2H, m) | 3.15(2H, d) |
| 3.79(3H, s) | 6.28(1H, dt) |
| 6.80(1H, d) | 6.8–6.9(1H, m) |
| 6.92(2H. s) | 7.1–7.4(11H. m) |

COMPOUND 44

4-(5H-Dibenzo[a,d]cyclohepten-5-ylidene)-1-(3-methoxycinnamyl)piperidine

| TLC(CHC13:MeOH=9:1) | Rf=0.89 |
|---|---|
| MS | 419(M+) |
| NMR | |
| 2.1–2.2(4H, m) | 2.2–2.4(2H, m) |
| 2.5–2.7(2H, m) | 3.12(2H, d) |
| 3.78(3H, s) | 6.23(1H, dt) |
| 6.42(1H, d) | 6.7–6.9(4H, m) |
| 6.92(2H, s) | 7.2–7.4(8H, m) |

COMPOUND 45

4-(5H-Dibenzo[a,d]cyclohepten-5-ylidene)-1-(4-methoxycinnamyl)piperidine

| TLC(CHC13:MeOH=9:1) | Rf=0.85 |
|---|---|
| MS | 419(M+) |
| NMR | |
| 2.1–2.2(4H, m) | 2.3–2.4(2H, m) |
| 2.6–2.7(2H, m) | 3.12(2H, d) |
| 3.79(3H, s) | 6.12(1H, dt) |
| 6.41(1H, d) | 6.83(2H, d) |

| | |
|---|---|
| 6.91(2H, s) | 7.1–7.3(10H, m) |

COMPOUND 46

4(10,11-Dihydro-5H-dibenzo[a,d]cyclohepten-5-ylidene)-1-(4-nitrocinnanyl)piperidine

| TLC(CHC13:MeOH=9:1) | Rf=0.93 |
|---|---|
| MS | 436(M+) |
| NMR | |
| 2.7–3.0(8H, m) | 3.3–3.4(4H, m) |
| 3.75(2H, d) | 6.7–6.8(2H, m) |
| 7.0–7.2(8H, m) | 7.5–7.6(2H, m) |
| 8.1–8.2(2H, m) | |

COMPOUND 47

1-(4-Aminocinnamyl)-4-(10,11-dihydro-5H-dibenzo[a,d]cyclohepten-5-ylidene)piperidine

| TLC(CHC13:MeOH=9:1) | Rf=0.64 |
|---|---|
| MS | 405(M+) |
| NMR | |
| 2.4–2.5(4H, m) | 2.6–2.7(2H, m) |
| 2.81(2H, dt) | 3.12(2H, d) |
| 3.3–3.4(2H, dt) | 3.67(2H, bs) |
| 6.08(1H, dt) | 6.39(1H, d) |
| 6.60(2H, d) | 7.0–7.2(10, m) |

COMPOUND 48

1-(4-Acethylaminocinnamyl)-4-(10,11-dihydro-5H-dibenzo[a,d]cyclohepten-5-ylidene)piperidine

| TLC(CHC13:MeOH=9:1) | Rf=0.54 |
|---|---|
| MS | 448(M+) |
| NMR | |
| 2.4–2.6(4H, m) | 2.7–2.8(8H, m) |
| 3.21(2H, d) | 6.21(1H, dt) |
| 6.44(1H, d) | 7.0–7.2(8H, m) |
| 7.34(2H, d) | 7.44(2H, d) |

COMPOUND 49

4-(5H-Dibenzo[a,d]cyclohepten-5-ylidene)-1-(4-fluorocinnamyl)piperidine

| TLC(CHC13:MeOH=9:1) | Rf=0.88 |
|---|---|
| MS | 445(M+) |
| NMR | |
| 2.1–2.2(4H, m) | 2.3–2.4(2H, m) |
| 2.6–2.8(2H, m) | 3.09(2H, d) |
| 6.17(1H, dt) | 6.42(1H, d) |
| 6.87(2H, s) | 6.9–7.0(2H, m) |
| 7.2–7.3(10H, m) | |

COMPOUND 50

3-[4-(5H-Dibenzo[a,d]cyclohepten-5-ylidene)-1-piperidinyl]-1-(3-pyridyl)-1-propene

| TLC(CHC13:MeOH=9:1) | Rf=0.44 |
|---|---|
| MS | 390(M+) |
| NMR | |
| 2.1–2.2(4H, m) | 2.3–2.5(2H, m) |
| 2.55–2.65(2H, m) | 3.09(2H, d) |
| 6.31(1H, dt) | 6.43(1H, d) |

| | |
|---|---|
| 6.90(2H, s) | 7.1–7.3(9H, m) |
| 7.62(1H, d) | 8.41(1H, dd) |
| 8.54(1H, d) | |

COMPOUND 51

4-(5H-Dibenzo[a,d]cyclohepten-5-ylidene)-1-(4-hydroxycinnamyl)piperidine

| TLC(CHC13:MeOH=9:1) | Rf=0.55 |
|---|---|
| MS(FAB.m/z) | 406(MH+) |
| NMR | |
| 2.1–2.3(4H, m) | 2.3–2.5(2H, m) |
| 2.6–2.8(2H, m) | 3.07(2H, d) |
| 5.97(1H, dt) | 6.37(1H, d) |
| 6.63(2H, d) | 6.87(2H, s) |
| 7.0–7.3(11H, m) | |

COMPOUND 52

1-(4-Acetoxycinnamyl)-4-(5H-dibenzo[a,d]cyclohepten-5-ylidene)piperidine

| TLC(CHC13:MeOH=9:1) | Rf=0.87 |
|---|---|
| MS | 447(M+) |
| NMR | |
| 2.1–2.2(4H, m)2.29(3H, s) | |
| 2.3–2.4(2H, m) | 2.6–2.7(2H, m) |
| 3.12(2H, d) | 6.21(1H, dt) |
| 6.43(1H, d) | 6.92(2H, s) |
| 6.9–7.0(2H, m) | 7.2–7.4(10H, m) |

COMPOUND 53

4-(5H-Dibenzo[a,d]cyclohepten-5-ylidene)-1-(4-hydroxy-3-methoxycinnamyl)piperidine

| TLC(CHC13:MeOH=9:1) | Rf=0.87 |
|---|---|
| MS | 435(M+) |
| NMR | |
| 2.1–2.2(4H, m) | 2.3–2.4(2H, m) |
| 2.6–2.7(2H, m) | 3.08(2H, d) |
| 3.81(3H, s) | 6.09(1H, dt) |
| 6.39(1H, d) | 6.78(1H, s) |
| 6.8–6.9(2H, m) | 6.87(2H, s) |
| 7.1–7.3(9H, m) | |

COMPOUND 54

1-(4-Acetoxy-3-methoxycinnamyl)-4-(5H-dibenzo[a,d]cyclohepten-5-ylidene)piperidine

| TLC(CHC13:MeOH=9:1) | Rf=0.83 |
|---|---|
| MS | 447(M+) |
| NMR | |
| 2.1–2.2(4H, m) | 2.29(3H, s) |
| 2.3–2.4(2H, m) | 2.6–2.7(2H, m) |
| 3.09(2H, d) | 3.81(3H, s) |
| 6.08(1H, dt) | 6.38(1H, d) |
| 6.80(2H, s) | 6.9–7.4(11H, m) |
| 7.2–7.4(9H, m) | |

COMPOUND 55

4-(5H-Dibenzo[a,d]cyclohepten-5-ylidene)-1-(3-hydroxycinnamyl)piperidine

| TLC(CHC13:MeOH=9:1) | Rf=0.45 |
|---|---|
| MS | 405(M+) |
| NMR(CD3OD) | |
| 2.10-2.30(4H, m) | 2.31-2.50(2H, m) |
| 2.70(2H, m) | 3.16(2H, d) |
| 6.42(1H, m) | 6.70(1H, m) |
| 6.84-6.95(2H, m) | 6.95(2H, s) |
| 7.10-7.38(10H, m) | |

COMPOUND 56

1-(3-Acetoxycinnamyl)-4-(5H-dibenzo[a,d]cyclohepten-5-ylidene)piperidine

| TLC(CHC13:MeOH=9:1) | Rf=0.80 |
|---|---|
| MS | 447(M+) |
| NMR | |
| 2.13-2.24(4H, m) | 2.30-2.45(2H, m) |
| 2.62(2H, m) | 3.14(2H, d) |
| 6.28(1H, m) | 6.43(1H, d) |
| 6.92(2H, s) | 6.92-6.97(1H, m) |
| 7.04(1H, s) | 7.18-7.35(10H, m) |

COMPOUND 57

4-(5H-Dibenzo[a,d]cyclohepten-5-ylidene)-1-[3-(2-methoxyacetoxy)cinnamyl]piperidine

| TLC(CHC13:MeOH=9:1) | Rf=0.65 |
|---|---|
| MS | 477(M+) |
| NMR(hydrochloride) | |
| 2.21-2.40(2H, m) | 2.48-2.60(4H, m) |
| 2.92-3.15(2H, m) | 3.20-3.65(2H, m) |
| 3.54(3H, s) | 4.26(2H, s) |
| 6.40-6.60(2H, m) | 6.92(2H, s) |
| 7.00-7.39(12H, m) | |

COMPOUND 58

4-(5H-Dibenzo[a,d]cyclohepten-5-ylidene)-1-(2-methoxycarbonylcinnamyl)piperidine

| TLC(CHC13:MeOH=9:1) | Rf=0.55 |
|---|---|
| MS | 447(M+) |
| NMR | |
| 2.52-2.68(4H, m) | 2.92-3.10(2H, m) |
| 3.30-3.50(2H, m) | 3.62(2H, d) |
| 6.42(1H, dt) | 6.91(2H, s) |
| 7.18(1H, d) | 7.24-7.40(8H, m) |
| 7.42-7.60(3H, m) | 7.90-7.95(1H, m) |

COMPOUND 59

4-(5H-Dibenzo[a,d]cyclohepten-5-ylidene)-1-(4-methoxycarbonylcinnamyl)piperidine

| TLC(CHC13:MeOH=9:1) | Rf=0.50 |
|---|---|
| MS | 447(M+) |
| NMR | |
| 2.15-2.24(4H, m) | 2.32-2.45(2H, m) |
| 2.60-2.68(2H, m) | 3.16(2H, d) |
| 3.90(3H, s) | 6.39(1H, dt) |
| 6.50(1H, d) | 6.92(2H, s) |
| 7.20-7.36(8H, m) | 7.37-7.41(2H, m) |

-continued

| | |
|---|---|
| 7.96-8.00(1H, m) | |

COMPOUND 60

4-(5H-Dibenzo[a,d]cyclohepten-5-ylidene)-1-(3-methoxy-2-nitrocinnamyl)piperidine

| TLC(HEXANOE:EtOAc=1:1) | Rf=0.30 |
|---|---|
| MS | 464(M+) |
| NMR | |
| 2.1-2.23(3H, m) | 2.24-2.42(2H, m) |
| 2.43-2.7(3H, m) | 3.07(2H, d) |
| 3.81(3H, s) | 6.37(2H, s) |
| 6.8-7.0(3H, m) | 7.05-7.4(10H, m) |

COMPOUND 61

4-(5H-Dibenzo[a,d]cyclohepten-5-ylidene)-1-(4-ethoxycarboxycinnamyl)piperidine

| TLC(CHC13:MeOH=9:1) | Rf=0.83 |
|---|---|
| MS | 477(M+) |
| NMR | |
| 1.23(3H, t) | 2.1-2.2(4H, m) |
| 2.3-2.4(2H, m) | 2.5-2.7(2H, m) |
| 3.13(2H, d) | 4.18(2H, q) |
| 6.24(1H, d) | 6.43(1H, d) |
| 6.90(2H, s) | 7.0-7.1(2H, m) |
| 7.1-7.4(10H, m) | |

COMPOUND 62

4-(5H-Dibenzo[a,d]cyclohepten-5-ylidene)-1-(4-methoxyacethoxycinnamyl)piperidine

| TLC(CHC13:MeOH=9:1) | Rf=0.75 |
|---|---|
| MS | 477(M+) |
| NMR | |
| 2.0-2.2(4H, m) | 2.4-2.6(2H, m) |
| 2.5-2.7(2H, m) | 3.17(2H, d) |
| 3.52(3H, s) | 4.24(2H, s) |
| 6.22(1H, dt) | 6.44(1H, d) |
| 6.95(2H, s) | 7.0-7.4(12H, m) |

COMPOUND 63

4-(5H-Dibenzo[a,d]cyclohepten-5-ylidene)-1-(3,4-dihydroxycinnamyl)piperidine

| TLC(CHC13:MeOH=9:1) | Rf=0.35 |
|---|---|
| MS(FAB.m/z) | 422(M+) |
| NMR | |
| 2.0-2.3(4H, m) | 2.4-2.6(2H, m) |
| 2.6-2.8(2H, m) | 3.17(2H, dt) |
| 6.27(1H, dt) | 6.41(1H, d) |
| 6.87(2H, s) | 6.9-7.5(13H, m) |

COMPOUND 64

4-Dibenzo[b,e]thiepin-11(6H)-ylidene-1-(2,4-dimethoxycinnamyl)piperidine

| TLC(CHC13:MeOH=9:1) | Rf=0.75 |
|---|---|
| MS | 469(M+) |

COMPOUND 65

4-(10,11-Dihydro-5H-dibenzo[a,d]cyclohepten-5-ylidene)-1-(2,4-dimethoxycinnamyl)piperidine

| TLC(CHC13:MeOH=9:1) | Rf=0.71 |
|---|---|
| MS | 451(M+) |

COMPOUND 66

1-(4-Aminosulfonylcinnamyl)-4-dibenzo[b,e]oxepin-11(6H)-ylidenepiperidine

| TLC(CHC13:MeOH=9:1) | Rf=0.32 |
|---|---|
| MS | 475(M+) |

COMPOUND 67

1-(4-Aminosulfonylcinnamyl)-4-(9-thioxanthylidene)-piperidine

| TLC(CHC13:MeOH=9:1) | Rf=0.35 |
|---|---|
| MS | 475(M+) |

COMPOUND 68

1-(4-Aminosulfonylcinnamyl)-4-(9-xanthylidene)piperidine

| TLC(CHC13:MeOH=9:1) | Rf=0.31 |
|---|---|
| MS | 458(M+) |

COMPOUND 69

1-(4-Aminosulfonylcinnamyl)-4-diphenylmethylenepiperidine

| TLC(CHC13:MeOH=9:1) | Rf=0.31 |
|---|---|
| MS | 444(M+) |

COMPOUND 70

1-(4-Aminosulfonylcinnamyl)-4-(10,11-dihydro-5H-dibenzo[a,d]cyclohepten-5-ylidene)piperidine

| TLC(CHC13:MeOH=9:1) | Rf=0.34 |
|---|---|
| MS | 471(M+) |

COMPOUND 71

1-(4-Aminosulfonyl-α-methylcinnamyl)-4-(5H-dibenzo[a,d]cyclohepten-5-ylidene)piperidine

| TLC(CHC13:MeOH=9:1) | Rf=0.29 |
|---|---|
| MS | 483(MH+) |

COMPOUND 72

1-(4-Aminosulfonyl-β-methylcinnamyl)-4-(5H-dibenzo[a,d]cyclohepten-5-ylidene)piperidine

| TLC(CHC13:MeOH=9:1) | Rf=0.45 |
|---|---|
| MS | 483(MH+) |

COMPOUND 73

1-(2-Chlorobenzyl)-4-(5H-dibenzo[a,d]cyclohepten-5-ylidene)piperidine

| MS | 397(M+) |
|---|---|
| H-NMR | |
| 2.1–2.8(8H, m) | 3.63(2H, bs) |
| 6.90(2H, s) | 7.1–7.3(12H, m) |

COMPOUND 74

1-Cyclohexyl-3-[4-(5H-dibenzo[a,d]cyclohepten-5-ylidene)1-piperidinyl]propane Yield 94%

| MS | 397(M+) |
|---|---|
| H-NMR | |
| 0.8–2.1(15H, m) | 2.47(2H, dd) |
| 2.68(2H, d) | 2.7–2.9(2H, m) |
| 3.0(2H, dd) | 3.49(2H, d) |
| 6.94(2H, s) | 7.1–7.4(8H, m) |

COMPOUND 75

1-Cyclohexyl-4-[4-(5H-dibenzo[a,d]cyclohepten-5-ylidene)-1-piperidinyl]butane Yield 72%

| MS | 411(M+) |
|---|---|
| H-NMR | |
| 0.8–2.1(15H, m) | 2.47(2H, dd) |
| 2.68(2H, d) | 2.7–2.9(2H, m) |
| 3.0(2H, dd) | 3.49(2H, d) |
| 6.92(2H, s) | 7.1–7.4(8H, m) |

COMPOUND 76

4-(5H-Dibenzo[a,d]cyclohepten-5-ylidene)-1-hexyl-piperidine Yield 95.6%

| TLC(CHC13:MeOH=9:1) | Rf=0.68 |
|---|---|
| MS | 357(M+) |
| H-NMR(CDCL3) | |
| 0.85(3H, d, J=8Hz) | 1.2–1.4(6H, m) |
| 1.7–1.9(2H, m) | 2.31(2H, dd, J=12, 8Hz) |
| 2.53(2H, d, J=12Hz) | 2.7–2.8(2H, m) |
| 3.14(2H, td, J=8, 3Hz) | 3.40(2H, d, J=12Hz) |
| 6.92(2H, s) | 7.2–7.4(8H, m) |

COMPOUND 77

1-Decyl-4-(5H-dibenzo[a,d]cyclohepten-5-ylidene)-piperidine Yield 66.7%

| TLC(CHC13:MeOH=9:1) | Rf=0.75 |
|---|---|
| MS | 413(M+) |
| NMR(hydrochloride) | |
| 0.85(3H, t, J=8Hz) | 1.2–1.4(14H, m) |
| 1.7–1.9(2H, m) | 2.33(2H, dd, J=12, 8Hz) |
| 2.54(2H, d, J=12Hz) | 2.7–2.8(2H, m) |

-continued

| | |
|---|---|
| 3.15(2H, td, J=8, 3Hz) | 3.39(2H, d, J=12Hz) |
| 6.92(2H, s) | 7.1-7.4(8H, m) |

COMPOUND 78

5-[4-(5H-Dibenzo[a,d]cyclohepten-5-ylidene)1-piperidinyl]2-(3,4-dichlorophenyl-2-isopropylvaleronitrile Yield 69.1%

| | |
|---|---|
| TLC(CHC13:MeOH=9:1) | Rf=0.60 |
| MS | 542(M+) |
| H-NMR(CDCL3) | |
| 0.77(3H, d, J=8Hz) | 1.18(3H, d, J=8Hz) |
| 2.0-3.4(15H, m) | 6.90(2H, s) |
| 7.18(H, dd, J=9, 2Hz) | 7.2-7.4(8H, m) |
| 7.48(1H, d, J=9Hz) | 7.53(1H, s) |

COMPOUND 79

4-(5-H-Dibenzo[a,d]cyclohepten-5-ylidene)-1-(3-[2-(cinnamoylamino)phenylthio]-1-propyl)piperidine

| | |
|---|---|
| TLC(CHC13:MeOH=9:1) | Rf=0.66 |
| MS | 568(M+) |
| H-NMR(CDCL3) | |
| 1.73(2H, tt, J=7, 7Hz) | 2.0-2.2(4H, m) |
| 2.3-2.4(2H, m) | 2.38(2H, t, J=7Hz) |
| 2.5-2.6(2H, m) | 2.78(2H, t, J=7Hz) |
| 6.59(1H, d, J=16Hz) | 6.88(2H, s) |
| 7.08(1H, tt, J=8, 1Hz) | 7.1-7.4(12H, m) |
| 7.5-7.6(3H, m) | 7.76(1H, d, J=16Hz) |
| 8.55(1H, d, J=8Hz) | 8.78(1H, bs, NH) |

COMPOUND 80

4-(5H-Dibenzo[a,d]cyclohepten-5-ylidene)-1-cinnamyl-piperidine

| | |
|---|---|
| TLC(CHC13:MeOH=9:1) | Rf=0.69 |
| MS | 389(M+) |
| H-NMR(CDCL3) | |
| 2.1-2.3(4H, m) | 2.4-2.5(2H, m) |
| 2.6-2.7(2H, m) | 3.14(2H, d, J=7Hz) |
| 6.26(2H, dt, J=16, 7Hz) | 6.48(2H, d, J=16Hz) |
| 6.92(2H, s) | 7.1-7.4(8H, m) |

COMPOUND 81

5-[4-(5H-Dibenzo[a,d]cyclohepten-5-ylidene)-1-piperidinyl]2,2-diphenylvaleronitrile Yield 57.7%

| | |
|---|---|
| TLC(CHC13:MeOH=9:1) | Rf=0.74 |
| MS | 506(M+) |
| H-NMR(CDCL3) | |
| 1.5-1.7(2H, m) | 2.0-2.2(4H, m) |
| 2.3-2.6(8H, m) | 6.87(2H, s) |
| 7.1-7.4(18H, m) | |

COMPOUND 82

5-[4-(5H-Dibenzo[a,d]cyclohepten-5-ylidene)-1-piperdinyl]-2-(3-trifluoromethylphenyl)-2-isopropylvaleronitrile Yield 47.5%

| | |
|---|---|
| TLC(CHC13:MeOH=9:1) | Rf=0.75 |
| MS | 540(M+) |
| H-NMR(CDCL3) | |

-continued

| | |
|---|---|
| 0.76(3H, d, J=7Hz) | 1.0-1.2(1H, m) |
| 1.5-1.6(1H, m) | 1.9-2.5(13H, m) |
| 6.88(2H, s) | 7.1-7.3(8H, m) |
| 7.48(1H, d, J=8Hz) | 7.56(1H, d, J=8Hz) |
| 7.59(1H, s) | |

COMPOUND 83

4-(5H-Dibenzo[a,d]cyclohepten-5-ylidene)-1-(2-fluorobenzyl)piperidine

| | |
|---|---|
| TLC(CHC13:MeOH=9:1) | Rf=0.75 |
| MS | 381(M+) |
| H-NMR(CDCL3) | |
| 2.1-2.2(4H, m) | 2.3-2.4(2H, m) |
| 2.5-2.6(2H, m) | 3.53(2H, s) |
| 6.88(2H, s) | 6.96(1H, dd, J=8, 8Hz) |
| 7.04(1H, dd, J=7, 7Hz) | 7.1-7.4(10H, m) |

COMPOUND 84

5-(5H-Dibenzo[a,d]cyclohepten-5-ylidene)-1-(4-fluorophenylethyl)piperidine

| | |
|---|---|
| TLC(CHC13:MeOH=9:1) | Rf=0.55 |
| MS | 395(M+) |
| H-NMR(CDCL3) | |
| 2.1-2.8(12H, m) | 6.9-7.4(2H, m) |

COMPOUND 85

5-[4-(5H-Dibenzo[a,d]cyclohepten-5-ylidene)-1-piperidinyl]-2-(3-trifluoromethylphenyl)valeronitrile

| | |
|---|---|
| TLC(CHC13:MeOH=9:1) | Rf=0.56 |
| Ms | 498(M+) |
| H-NMR(CDCL3) | |
| 1.5-2.7(14H, m) | 3.97(1H, t, J=7Hz) |
| 6.90(2H, s) | 7.1-7.6(12H, m) |

COMPOUND 86

1-(3-Aminobenzyl)-4-(5H-dibenzo[a,d]cyclohepten-5-ylidene)piperidine

| | |
|---|---|
| TLC(CHCl3:MeOH=9:1) | Rf=0.62 |
| MS | 378(M+) |
| H-NMR(CDCL3) | |
| 2.1-2.8(8H, m) | 3.50(2H, s) |
| 3.4-3.8(2H, bs) | 6.5-6.8(2H, m) |
| 6.93(2H, s) | 7.0-7.4(10H, m) |

COMPOUND 87

4-[4-(4H-Dibenzo[a,d]cyclohepten-5-ylidene)-1-piperidinyl]-3',4'-dimethoxybutyrophenone

| | |
|---|---|
| TLC(CHCl3:MeOH=9:1) | Rf=0.52 |
| MS | 479(M+) |
| H-NMR(CDCL3) | |
| 1.8-2.6(12H, m) | 2.95(2H, t, J=8Hz) |
| 3.93(3H, s) | 3.96(3H, s) |
| 6.85(1H, d, J=10Hz) | 6.88(2H, s) |
| 7.2-7.4(8H, m) | 7.5-7.7(2H, m) |

COMPOUND 88

1-(4-Cyanobenzyl)-4-(5H-dibenzo[a,d]cyclohepten-5-ylidene)-1-piperidine

| TLC(CHCl3:MeOH=9:1) | Rf=0.70 |
|---|---|
| MS(FD.m/z) | 388(M+) |
| H-NMR | |
| 2.2–2.5(2H, m) | 2.5–2.8(2H, m) |
| 3.0–3.4(4H, m) | 4.03(2H, d) |
| 6.92(2H, s) | 7.1–8.0(12H, m) |

COMPOUND 89

1-Cyclohexyl-4-[4-(10,11-dihydro-5H-dibenzo[a,d]cyclohepten-5-ylidene)-1-piperidinyl]butane

| TLC(HEXANE.:EtOAc=1:1) | Rf=0.67 |
|---|---|
| MS | 413(M+) |
| H-NMR | |
| 0.80–0.88(2H, m) | 1.10–1.73(15H, m) |
| 2.12–2.19(2H, m) | 2.28–2.30(2H, m) |
| 2.32–2.47(4H, m) | 2.64–2.69(2H, m) |
| 2.77–2.86(2H, m) | 3.36–3.45(2H, m) |
| 7.05–7.15(8H, m) | |

COMPOUND 90

Cyclohexyl-[4-(5H-dibenzo[a,d]cyclohepten-5-ylidene)-1-piperidinyl]methane

| TLC(CHCl3:MeOH=9:1) | Rf=0.58 |
|---|---|
| MS(FD.m/z) | 369(M+) |
| H-NMR | |
| 0.7–2.9(20H, m) | 6.91(2H, s) |
| 7.05–7.4(8H, m) | |

COMPOUND 91

4-(5H-Dibenzo[a,d]cyclohepten-5-ylidene)-1-(2,3-dimethoxybenzyl)piperidine

| TLC(CHCl3:MeOH=9:1) | Rf=0.63 |
|---|---|
| MS(FD.m/z) | 423(M+) |
| H-NMR | |
| 2.0–2.8(10H, m) | 3.80(3H, s) |
| 3.84(3H, s) | 6.7–7.4(11H, m) |
| 6.89(2H, s) | |

COMPOUND 92

3-Cyanopropyl-4-(5H-dibenzo[a,d]cyclohepten-5-ylidene)piperidine NMR

| 1.62–2.72(14H, m) | 6.92(2H, s) |
|---|---|
| 7.10–7.30(8H, m) | |

COMPOUND 93

4-(5H-Dibenzo[a,d]cyclohepten-5-ylidene)-1-(3,4-dimethoxyphenacyl)piperidine

| MS | 451(M+) |
|---|---|
| NMR | |
| 2.15–2.30(4H, m) | 2.37–2.45(2H, m) |
| 2.65–2.75(2H, m) | 3.70(2H, s) |
| 3.90(3H, s) | 3.92(3H, s) |
| 6.85(1H, d) | 6.90(2H, s) |
| 7.18–7.34(8H, m) | 7.59(1H, d) |
| 7.66(1H, dd) | |

COMPOUND 94

1-Cyclohexyl-6-[4-(5H-dibenzo[a,d]cyclohepten-5-ylidene)-1-piperidinyl]hexane

| TLC(CHCl3:MeOH=9:1) | Rf=0.65 |
|---|---|
| MS(FD.m/z) | 439(M+) |
| H-NMR | |
| 0.8–1.0(2H, m) | 1.1–1.4(10H, m) |
| 1.5–1.7(8H, m) | 2.2–2.4(1H, m) |
| 2.5–2.9(5H, m) | 3.0–3.2(2H, m) |
| 3.4–3.6(3H, m) | 6.92(2H, s) |
| 7.1–7.4(8H, m) | |

COMPOUND 95

1-(4-Cyclohexylbutyl)-4-(9-thioxanthylidene)piperidine

| TLC(CHCl3:MeOH=9.1) | Rf=0.69 |
|---|---|
| MS(FD.m/z) | 417(M+) |
| H-NMR | |
| 0.8–1.0(2H, m) | 1.1–1.4(9H, m) |
| 1.5–1.7(6H, m) | 2.2–2.4(2H, m) |
| 2.5–2.6(2H, m) | 2.8–2.9(2H, m) |
| 2.9–3.1(6H, m) | 7.1–7.5(8H, m) |

COMPOUND 96

1-(4-Cyclohexylbutyl)-4-(9-xanthylidene)piperidine

| TLC(CHCl3:MeOH=9:1) | Rf=0.74 |
|---|---|
| H-NMR | |
| 0.8–1.0(2H, m) | 1.1–1.4(9H, m) |
| 1.5–1.7(6H, m) | 2.3–2.4(2H, m) |
| 2.52(4H, t) | 2.91(4H, t) |
| 7.0–7.4(8H, m) | |

COMPOUND 97

5-[4-(4-Fluorobenzoyl)-1-piperidinyl]-2-isopropyl-2-(3,4,5-trimethoxyphenyl)valeronitrile

| TLC(CHCl3:MeOH=9:1) | Rf=0.56 |
|---|---|
| MS | 497(M+) |
| H-NMR(CDCL3) | |
| 0.76(3H, bs) | 1.0–1.2(1H, m) |
| 1.16(3H, bs) | 1.4–2.5(12H, m) |
| 2.9–3.4(3H, m) | 3.82(3H, s) |
| 3.87(3H, s) | 6.6–6.8(2H, m) |
| 6.6–6.8(2H, m) | 7.0–7.2(2H, m) |
| 7.8–8.1(2H, m) | |

COMPOUND 98

2-(3,4-Dimethoxyphenyl)-2-dodecyl-5-[4-(4-fluorobenzoyl)-1-piperidinyl]valeronitrile

| TLC(CHCl3:MeOH=9:1) | Rf=0.70 |
|---|---|
| MS | 592(M+) |
| H-NMR(DMSO-d6) | |
| 0.84(3H, t, J=8Hz) | 1.2–1.5(22H, m) |
| 1.8–2.1(8H, m) | 2.9–3.1(4H, m) |

-continued

| | |
|---|---|
| 3.4–3.5(2H, m) | 3.6–3.8(1H, m) |
| 3.76(3H, s) | 3.79(3H, s) |
| 6.9–7.0(3H, m) | 7.40(2H, dd, j=8, 8Hz) |
| 8.07(2H, dd, J=10, 8Hz) | |

COMPOUND 99

5-[4-(3,4-Dimethoxybenzoyl)-1-piperidinyl]-2-(3,4-dimethoxyphenyl)-2-isopropylvaleronitrile

| | |
|---|---|
| TLC(CHCl3:MeOH=9:1) | Rf=0.83 |
| MS | 508(M+) |
| H-NMR(CDCL3) | |
| 0.80(3H, t, J=6Hz) | 1.21(3H, t, J=6Hz) |
| 2.0–3.8(16H, m) | 3.89(3H, s) |
| 3.93(3H, s) | 3.96(6H, s) |
| 6.86(1H, d, J=8Hz) | 6.91(1H, d, J=8Hz) |
| 6.94(1H, d, J=2Hz) | 7.00(1H, dd, J=8, 2Hz) |
| 7.44(1H, d, J=2Hz) | 7.49(1H, dd, J=8, 2Hz) |

COMPOUND 100

5-{4-[Bis(4-fluorophenyl)methylene]-1-piperidinyl}-2-(3,4-dimethoxyphenyl)-2-isopropylvaleronitrile

| | |
|---|---|
| TLC(CHCl3:MeOH=9:1) | Rf=0.54 |
| MS | 544(M+) |
| H-NMR(CDCL3) | |
| 0.78(3H, d, J=8Hz) | 1.20(3H, d, J=8Hz) |
| 1.6–3.6(15H, m) | 3.87(3H, s) |
| 3.94(3H, s) | 6.8–7.1(11H, m) |

COMPOUND 101

2-(3,4-Dimethoxyphenyl)-2-isopropyl-5-[4-(2,4,6-trimethylbenzoyl)-1-piperidinyl]valeronitrile

| | |
|---|---|
| TLC(CHCl3:MeOH=9:1) | Rf=0.64 |
| MS | 490(M+) |
| H-NMR(CDCL3) | |
| 0.8–1.3(6H, m) | 1.9–3.6(25H, m) |
| 3.9–4.0(6H, m) | 6.8–7.0(5H, m) |

COMPOUND 102

2-(3,4-Dimethoxyphenyl)-5-[4-(4-fluorobenzoyl)-1-piperazinyl]-2-isopropylvaleronitrile

| | |
|---|---|
| TLC(CHCl3:MeOH=9:1) | Rf=0.70 |
| MS | 421(M+) |
| H-NMR(CDCL3) | |
| 0.81(3H, d, J=7Hz) | 1.22(3H, d, J=7Hz) |
| 1.5–1.7(2H, m) | 2.15(1H, qq, J=7, 7Hz) |
| 2.2–2.5(2H, m) | 3.0–3.6(10H, m) |
| 3.89(3H, s) | 3.95(3H, s) |
| 6.88(2H, d, J=8Hz) | 6.95(2H, d, J=2Hz) |
| 7.04(2H, dd, J=8, 2Hz) | 7.1–7.2(3H, m) |
| 7.37(2H, dd, J=8, 8Hz) | |

COMPOUND 103

5-[4-(4-Fluorobenzoyl)-1-piperindyl]-2-phenylvaleronitrile

| | |
|---|---|
| TLC(CHCl3:MeOH=9:1) | Rf=0.54 |
| MS | 364(M+) |
| H-NMR(CDCL3) | |
| 1.6–1.8(2H, m,) | 1.8–1.9(4H, m) |
| 1.9–2.0(2H, m) | 2.0–2.2(2H, m) |
| 2.41(2H, t, J=7Hz) | 2.9–3.0(2H, m) |
| 3.20(1H, m) | 3.88(1H, t, J=7Hz,) |
| 7.1–7.2(2H, m) | 7.3–7.4(5H, m,) |
| 7.9–8.0(2H, m) | |

COMPOUND 104

2-(3,4-Dimethoxyphenyl)-5-[4-(4-fluorophenyl)methylene-1-piperidinyl]-2-isopropylvaleronitrile

| | |
|---|---|
| TLC(CHCl3:MeOH=9:1) | Rf=0.73 |
| MS | 450(M+) |
| H-NMR(CDCL3) | |
| 0.80(3H, d, J=8Hz) | 1.20(3H, d, J=8Hz) |
| 1.5–3.6(15H, m) | 3.9–4.0(6H, m) |
| 6.4–6.5(1H, m) | 6.8–7.2(7H, m) |

COMPOUND 105

2-Butyl-2-(3,4-dimethoxyphenyl)-5-[4-(4-fluorobenzoyl)-1-piperidinyl]valeronitrile

| | |
|---|---|
| TLC(CHCl3:MeOH=9:1) | Rf=0.67 |
| MS | 480(M+) |
| H-NMR(CDCL3) | |
| 0.86(3H, t, J=8Hz) | 1.0–3.8(21H, m) |
| 3.88(3H, s) | 3.96(3H, s) |
| 6.87(1H, d, J=8Hz) | 6.92(1H, s) |
| 6.99(1H, d, J=8Hz) | 7.18(2H, dd, J=8, 8Hz) |
| 7.92(2H, dd, J=8.6Hz) | |

COMPOUND 106

5-[4-(4-Fluorobenzoyl)-1-piperdinyl]-2-isopropyl-2-(1-methylpyrrole-2-yl)valeronitrile

| | |
|---|---|
| TLC(CHCl3:MeOH=9:1) | Rf=0.54 |
| MS | 409(M+) |
| H-NMR(CDCL3) | |
| 1.00(3H, d, J=7Hz) | 1.08(3H, d, J=7Hz) |
| 1.4–1.5(1H, m, CH2CCN) | 1.5–1.7(1H, m, CH2CCN) |
| 1.7–1.9(4H, m) | 1.9–2.1(4H, m) |
| 2.24(1H, hept, J=7Hz) | 2.3–2.4(2H, m) |
| 2.8–2.9(2H, m) | 3.18(1H, pseud hept.) |
| 3.74(3H, s) | 6.00–6.03(1H, m) |
| 6.10–6.14(1H, m) | 6.52–6.54(1H, m) |
| 7.09–7.16(1H, m) | 7.93–7.98(2H, m) |

COMPOUND 107

[2-(2-Nitrobenzenesulfonyl)aminoethyl]-4-(4-fluorobenzoyl)piperidine

| | |
|---|---|
| MS(FAB, m/z) | 436(MH+) |
| NMR | |
| 1.80–2.05(5H, m) | 3.04–3.35(6H, m) |
| 3.56–3.65(2H, m) | 3.65–3.75(1H, m) |
| 7.90–7.95(2H, m) | 7.40(2H, dd, J=8, 8Hz) |
| 8.45(1H, bs) | 8.02–8.13(4H, m) |

COMPOUND 108

2-(3,4-Dimethoxyphenyl)-5-[4-(4-fluorobenzoyl)-1-piperidinyl]valeronitrile

| MS(m/z) | 424(M+) |
|---|---|
| NMR | |
| 1.8–2.4(8H, m) | 2.9–3.7(6H, m) |
| 3.85(3H, s) | 3.88(3H, s) |
| 3.8–4.4(2H, m) | 6.8–6.9(3H, m) |
| 7.1–7.2(2H, m) | 7.9–8.0(2H, m) |

COMPOUND 109

1-[2-(2-Ethoxycarbonylaminobenzenesulfonyl)aminoethyl]-4-(4-fluorobenzoyl)piperidine

| MS(FAB, m/z) | 478(MH+) |
|---|---|
| NMR | |
| 1.12(3H, t, J=8Hz) | 1.82–2.10(5H, m) |
| 3.12–3.27(2H, m) | 3.65–3.77(4H, m) |
| 4.10(2H, q, J=8Hz) | 4.23–4.30(2H, m) |
| 6.16(1H, br) | 6.68(1H, dd, J=8, 8Hz) |
| 6.89(1H, d, J=8Hz) | 7.36(1H, dd, J=8, 8Hz) |
| 7.40(2H, dd, J=8, 6Hz) | 7.59(1H, d, J=8Hz) |
| 8.10(2H, dd, J=8, 6Hz) | |

COMPOUND 110

Methyl 2-[N-methyl-N-2-[2,4-(1H,3H)-quinazolinedione-3-yl]-ethylamino]ethyl-2,6-dimethyl-4-(3-nitrophenyl)-1,4-dihydropyridine-3,5-dicarboxylate

| MS | 578(MH+) |
|---|---|
| NMR | |
| 2.30(3H, s) | 2.34(3H, s) |
| 2.38(3H, s) | 2.60–2.95(6H, m) |
| 3.83(3H, s) | 4.08(2H, t, J=7Hz) |
| 4.04(1H, s) | 5.86(1H, s) |
| 6.91(1H, dd, J=8, 8Hz) | 7.08(1H, dd, J=8, 8Hz) |
| 7.23(1H, dd, J=8, 8Hz) | 7.48(1H, dd, J=8, 8Hz) |
| 7.70(1H, d, J=8Hz) | 7.85(1H, d, J=8Hz) |
| 8.02(1H, s) | |

COMPOUND 111

1,3-Bis[4-(4-fluorobenzoylpiperidine-1-yl)propane

| NMR | |
|---|---|
| 1.65–2.22(12H, m) | 2.25–3.33(12H, m) |
| 7.02(4H, dd, J=8, 8Hz) | 7.88(4H, dd, J=8, 6Hz) |

COMPOUND 112

2-(3,4-Dimethoxyphenyl)-5-[4-(a-hydroxy-4-fluorobenzyl)-1-piperidinyl]-2-isopropylvaleronitrile

| MS | 469 |
|---|---|
| NMR | |
| 0.78(3H, dd, J=7Hz) | 1.1–1.2(4H, m) |
| 1.16(3H, d, J=7Hz) | 1.2–1.4(1H, m) |
| 1.4–1.6(2H, m) | 1.6–1.9(4H, m) |
| 2.0–2.1(2H, m) | 2.19(2H, pseud t, J=8Hz) |
| 2.6–2.9(2H, m) | 3.86(3H, s) |
| 3.87(3H, s) | 4.26(1H, d, J=7Hz) |
| 6.8–7.1(5H, m) | 7.1–7.3(2H, m) |

COMPOUND 113

2,2-Diphenyl-5-[4-(4-fluorobenzoyl)-1-piperidinyl]-valeronitrile

| NMR | |
|---|---|
| 1.9–2.1(4H, m) | 3.0–3.1(4H, m) |
| 3.2–3.3(2H, m) | 3.7–3.8(1H, m) |
| 7.18(2H, dd, J=8, 8Hz) | 7.2–7.5(10H, m) |
| 7.92(2H, dd, J=10, 8Hz) | |

COMPOUND 114

2-(3,4-Dimethoxyphenyl)-5-[4-(4-fluorobenzoyl)-1-piperidinyl]-2-octylvaleronitrile

| MS | 536(M+) |
|---|---|
| NMR | |
| 0.86(3H, d, J=8Hz) | 1.0–3.8(14H, m) |
| 3.88(3H, s) | 3.96(3H, s) |
| 6.87(1H, d, J=8, 2Hz) | 6.92(1H, d, J=2Hz) |
| 6.99(1H, dd, J=8, 2Hz) | 7.18(2H, dd, J=8, 8Hz) |
| 7.90(2H, dd, J=10, 8Hz) | |

COMPOUND 115

4-(4-Fluorobenzoyl)-1-[2-(N-phenylcarbamoylamino)ethyl]piperidine

| MS | 369(M+) |
|---|---|

EXAMPLES

Evaluation of antiarrhythmic activity of the compounds

EXAMPLE 1

Female Guinea Pigs, weighing 250–350 g, were anesthetized with urethane. The lead II ECG was continuously recorded.

Drugs, compound 1 and compound 2, were dissolved in the 2.5% nicol 2.5% ethanol solution, and injected into the femoral vein.

After 30 min of drug injection ouabain was infused intravenously through the left femoral vein at a rate of 10 ug/kg/min.

The time, ventricular premature contractions (VPC) ventricular fibrillation (VF) and cardiac arrest (CA) appeared on ECG, were measured, and the cumulative ouabain dosage to induce ventricular premature contractions, ventricular fibrillation and cardiac arrest, respectively, was calculated.

The results are summarized in Table 1.

EXAMPLE 2

Mongrel dogs of either sex, weighing 8–20 kg, were anesthetized with pentobarbitone sodium, 30 mg/kg. The lead II ECG, atrial electrogram from catheter tip electrodes in the right atrium, and blood pressure were continuously recorded. Ouabain 40 ug/kg was injected intravenously and with an additional 10 ug/kg every 20 min until stable ventricular arrhythmias were produced. The severity of arrhythmia was expressed by the arrhythmic ratio i.e. number of ventricular ectopic beats divided by the total heart rate. The arrhythmic ratio was calculated for 60 min after bolus intravenous administration.

The results are summarized in Table 2.

EXAMPLE 3

Mongrel dogs of either sex, weighing 8-20 kg, were anaesthetized initially with thiopentone sodium. After incubation, 1.0% halothane. vaporized with 100% 02, was administered with volume limited ventilator. Adrenaline was infused through the left femoral vein at the rate of 2.5-5 ug/kg/min. After 3 min of adrenaline infusion, drugs were injected into the right femoral vein. The lead II ECG, atrial electrogram from catheter tip electrodes in the right atrium and blood pressure were continuously recorded. The severity of ectopic beats divided by the total heart rate. The arrhythmic ratio was calculated for 15 min after drug administration.

The results are summarized in Table 3.

EXAMPLE 4

Three mice were subjected to one group experiment. Drugs were administered with intraperitoneal injection in three mice 30 min before deep chloroform anaesthesia. If less than two mice displayed cardiac arrhythmia or tachycardia, above 200 beats/min, when exposed to deep chloroform anaesthesia, the drug was judged as having an antiarrhythmic effect.

The results are summarized in Table 4.

TABLE 1

| Compound # | Dose (mg/kg) | VPC (μg/kg) | VF (μg/kg) | CA (μg/kg) |
|---|---|---|---|---|
| control |  | 153 | 221 | 324 |
| 9 | 1 | 169 | 236 | 294 |
| 10 | 1 | 166 | 245 | 304 |
| 11 | 1 | 163 | 256 | 304 |
| 13 | 1 | 169 | 253 | 299 |
| 14 | 1 | 144 | 333 | 416 |
| 16 | 1 | 172 | 217 | 273 |
| 17 | 1 | 184 | 275 | 380 |
| 18 | 1 | 203 | 330 | 395 |
| 20 | 1 | 181 | 366 | 420 |
| 21 | 1 | 163 | 334 | 393 |
| 22 | 1 | 178 | 346 | 409 |
| 23 | 0.3 | 142 | 442 | 499 |
| 24 | 1 | 168 | 250 | 306 |
| 25 | 1 | 155 | 269 | 326 |
| 27 | 1 | 163 | 255 | 309 |
| 28 | 1 | 150 | 291 | 348 |
| 29 | 1 | 159 | 288 | 344 |
| 30 | 1 | 145 | 279 | 358 |
| 31 | 1 | 113 | 271 | 349 |
| 32 | 1 | 212 | 308 | 374 |
| 33 | 1 | 152 | 606 | 646 |
| 34 | 1 | 125 | 556 | 579 |
| 35 | 1 | 159 | 342 | 413 |
| 36 | 1 | 149 | 344 | 399 |
| 37 | 1 | 160 | 298 | 368 |
| 38 | 1 | 175 | 357 | 427 |
| 39 | 1 | 254 | 334 | 422 |
| 40 | 1 | 170 | 321 | 372 |
| 41 | 1 | 152 | 295 | 357 |
| 42 | 1 | 225 | 386 | 454 |
| 43 | 1 | 203 | 372 | 469 |
| 44 | 3 | 205 | 617 | 656 |
| 45 | 1 | 147 | 335 | 389 |
| 46 | 1 | 180 | 347 | 431 |
| 47 | 1 | 240 | 265 | 351 |
| 48 | 1 | 212 | 247 | 334 |
| 49 | 1 | 140 | 311 | 380 |
| 51 | 1 | 146 | 259 | 344 |
| 52 | 3 | 205 | 441 | 476 |
| 53 | 3 | 202 | 398 | 458 |
| 54 | 1 | 193 | 264 | 350 |
| 55 | 1 | 175 | 320 | 374 |
| 56 | 3 | 187 | 254 | 309 |
| 57 | 1 | 136 | 280 | 346 |
| 58 | 3 | 174 | 384 | 448 |
| 59 | 1 | 203 | 367 | 419 |

TABLE 1-continued

| Compound # | Dose (mg/kg) | VPC (μg/kg) | VF (μg/kg) | CA (μg/kg) |
|---|---|---|---|---|
| 60 | 1 | 186 | 534 | 586 |
| 61 | 1 | 232 | 294 | 356 |
| 62 | 1 | 186 | 389 | 454 |
| 63 | 1 | 211 | 322 | 398 |
| 64 | 1 | 121 | 309 | 365 |
| 65 | 1 | 146 | 325 | 381 |
| 66 | 3 | 164 | 264 | 312 |
| 67 | 3 | 155 | 193 | 245 |
| 69 | 3 | 185 | 202 | 274 |
| 70 | 1 | 153 | 373 | 432 |
| 72 | 1 | 171 | 282 | 363 |
| 74 | 1 | 182 | 239 | 289 |
| 75 | 1 | 178 | 257 | 305 |
| 76 | 1 | 196 | 205 | 274 |
| 77 | 1 | 179 | 310 | 369 |
| 78 | 1 | 154 | 279 | 337 |
| 79 | 1 | 172 | 302 | 358 |
| 80 | 1 | 200 | 329 | 383 |
| 81 | 1 | 183 | 267 | 329 |
| 82 | 1 | 160 | 285 | 339 |
| 83 | 1 | 176 | 261 | 305 |
| 84 | 1 | 168 | 277 | 335 |
| 85 | 1 | 184 | 270 | 318 |
| 86 | 1 | 162 | 240 | 292 |
| 87 | 1 | 199 | 260 | 305 |
| 88 | 1 | 185 | 254 | 318 |
| 89 | 1 | 204 | 257 | 312 |
| 90 | 1 | 178 | 228 | 273 |
| 91 | 1 | 169 | 286 | 338 |
| 94 | 1 | 178 | 301 | 357 |
| 95 | 1 | 174 | 264 | 305 |
| 96 | 1 | 178 | 264 | 312 |
| 97 | 1 | 134 | 332 | 397 |
| 98 | 1 | 160 | 318 | 370 |
| 100 | 1 | 185 | 275 | 355 |
| 101 | 1 | 161 | 221 | 293 |
| 102 | 1 | 163 | 246 | 297 |
| 103 | 1 | 184 | 308 | 351 |
| 104 | 1 | 168 | 244 | 311 |
| 106 | 1 | 199 | 312 | 362 |

TABLE 2

| time after administration (min) | Arrhythmic Ratio Compound #23 30 ug/kg | Compound #75 300 ug/kg |
|---|---|---|
| 0 | 1.00 | 1.00 |
| 2 | 1.00 | 0.80 |
| 4 | 1.00 | 0.71 |
| 6 | 0.60 | 0.41 |
| 8 | 0.77 | 0.19 |
| 10 | 0.50 | 0.19 |
| 12 | 0.50 | 0.43 |
| 15 | 0.50 | 0.43 |
| 20 | 0.00 | 0.38 |
| 30 | 0.00 | 0.45 |
| 60 | 0.00 | 0.45 |

TABLE 3

| time after administration (min) | Arrhythmic Ratio Compound #23 10 ug/kg | Compound #75 300 ug/kg |
|---|---|---|
| 0 | 1.00 | 1.00 |
| 2 | 0.80 | 0.66 |
| 4 | 0.50 | 0.41 |
| 6 | 0.00 | 0.18 |
| 8 | 0.00 | 0.08 |
| 10 | 0.00 | 0.07 |
| 12 | 0.00 | 0.07 |
| 15 | 0.00 | 0.00 |

TABLE 4

| Compound # | minimum effective dose (mg/kg) |
|---|---|
| 107 | 100 |
| 108 | 50 |
| 109 | 100 |
| 110 | 100 |
| 111 | 100 |
| 112 | 100 |
| 113 | 10 |
| 114 | 25 |
| 115 | 50 |

We claim:

1. A method of reducing or eliminating cardiac arrhythmia, comprising administering orally or parenterally an effective amount of a piperidine derivative of formula (I) or a pharmaceutically acceptable salt thereof:

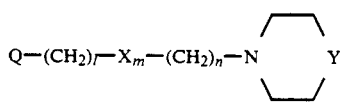

wherein

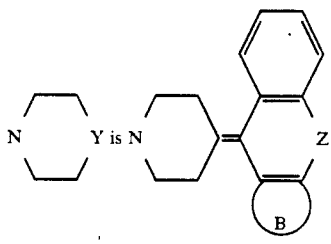

wherein
B is benzene;
Z is

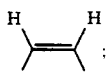

X is

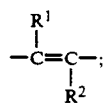

wherein $R^1$ and $R^2$ are the same or different and are independently selected from hydrogen, methyl, ethyl or propyl; Q is phenyl, cyclohexyl or 1-hexyl; from 1 to 3 hydrogen atoms in Q may be independently substituted by alkyl of from 1 to 3 carbon atoms, perfluoroalkyl of from 1 to 3 carbon atoms, acylamino of from 1 to 6 carbon atoms, perfluoroacylamino of from 1 to 3 carbon atoms, alkoxy of from 1 to 3 carbon atoms, alkanesulfonylamino of from 1 to 3 carbon atoms, perfluoroalkanesulfonylamino of from 1 to 3 carbon atoms, acetoxy of from 1 to 3 carbon atoms, aminocarbonyl, aminosulfonyl, fluoro, chloro, cyano, hydroxy, nitro, amino, imidazolylmethyl, cinnamoylamino, p-fluorobenzoyl, cyanomethyl, cyanoethyl, methoxyacetoxy or alkoxycarbonyl of from 1 to 3 carbon atoms;
1 is an integer of from 0 to 1;
m is an integer of from 0 to 1;
n is an integer of from 1 to 6.

2. A method of reducing or eliminating cardiac arrhythmia, comprising administering orally or parenterally an effective amount of a piperidine derivative, or pharmaceutically acceptable salt thereof, selected from the group consisting of:
4-(5H-dibenzo[a,d]cyclohepten-5-ylidene)-1-[4-H-imidazolylmethyl)cinnamyl)piperidine, 4-(5H-dibenzo[a,b]cyclohepten-5-ylidene)-1-(4-nitrocinnamyl)piperidine, 1-(4-aminocinnamyl)-4-(5H-dibenzo[a,d]cyclohepten-5-ylidene)piperidine, 1-(4-acetylaminocinnamyl)-4-(5H-dibenzo[a,d]cyclohepten-5-ylidene)piperidine, 3-[4-(5H-dibenzo[a,d]cyclohepten-5-ylidene]-1-piperidinyl]-1-(4-nitrophenyl)propane, 1-(4-aminophenyl)-3-[4-(5H-dibenzo[a,d]cyclohepten-5-ylidene)-1-piperidinyl]propane, 1,-(4-acetylaminophenyl)-3-[4-(5H-dibenzo[a,d]cyclohepten-5-ylidene)-1-piperidinyl]propane, N-[3-(5H-dibenzo[a,d]cyclohepten-5-ylidene)-1-piperidinyl]propanoyl-3,4-dimethoxyanilide 1-(N-acetyl-4-piperidinyl)-3-[4-(5H-dibenzo[a,]cyclohepten-5-ylidene)- 1-piperidinyl]propane, 4-(5H-dibenzo[a,d]cyclohepten-5-ylidene)-1-(2,4-dimethoxycinnamyl)piperidine, 1-(4-cyanocinnamyl)-4-(5H-dibenzo[a,d]cyclohepten-5-ylidene)-piperidine, 1-cyclohexyl-4-[4-(10,11-dihydroxy-5H-dibenzo[a,d]cyclohepten-5-ylidene)-1-piperidinyl)butane, 4-(5H-benzo[a,d]cyclohepten-5-ylidene)-1-(4-propanoylaminocinnamyl)piperidine, 4-(5H-dibenzo[a,d]cyclohepten-5-ylidene)-1-(4-ethoxycarbonylaminocinnamyl)piperidine, 4-(5H-dibenzo[a,d]cyclohepten-5-ylidene)-1-(4-methanesulfonylaminocinnamyl)piperidine, 4-(5H-dibenzo[a,d]cyclohepten-5-ylidene)-1-(3-methoxycarbonylcinnamyl)piperidine, 4-(5H-dibenzo[a,d]cyclohepten-5-ylidene)-1-(4-methoxycarbonylaminocinnamyl)piperidine, 4-(5H-dibenzo[a,d]cyclohepten-5-ylidene)-1-(4-pivaloylaminocinnamyl)piperidine, 4-(5H-dibenzo[a,d]cyclohepten-5-ylidene)-1-(4-trifluoroacetylaminocinnamyl)piperidine, 1-(4-butanoylaminocinnamyl)-4-(5H-dibenzo[a,d]cyclohepten-5-ylidene)piperidine, 1-(4-ethoxycarbonylaminocinnamyl)-4-(4-fluorobenzoyl)piperidine, 4-(4-fluorobenzoyl)-1-(4-methoxycarbonylaminocinnamyl)piperidine, 4-(4-fluorobenzoyl)-1-(4-propanoylaminocinnamyl)piperidine, 4-(4-fluorobenzoyl)-1-(4-trifluoroacetylaminocinnamyl)piperidine, 1-(4-acetylaminocinnamyl)-4-(4-fluorobenzoyl)piperidine, 1-(4-aminocinnamyl)-4-(4-fluorobenzoyl)piperidine, 4-(4-fluorobenzoyl)-1-(4-nitrocinnamyl)piperidine, 1-(4-aminocarbonylcinnamyl)-4-(5H-dibenzo[a,d]cyclohepten-5-ylidene)piperidine, 4-(5H-dibenzo[a,d]cyclohepten-5-ylidene)-1-(4-trifluoromethylcinnamyl)piperidine, 4-(5H-dibenzo[a,d]cyclohepten-5-ylidene)-1-(4-cyanomethylcinnamyl)piperidine, 4-(5H-dibenzo[a,d]cyclohepten-5-ylidene)-1-(3,4-dichlorocinnamyl)piperidine, 4-(5H-dibenzo[a,d]cyclohepten-5-ylidene)-1-(3,4-dimethoxy-2-nitrocinnamyl)piperidine, 4-(5H-dibenzo[a,d]-cyclohepten-5-ylidene)-1-(2,5-dimethoxycinnamyl)piperidine, 4-(5H-dibenzo[a,d]cyclohepten-5-ylidene)-1-(2,3- dimethoxycinnamyl)piperidine, 4-(5H-dibenzo[a,d]cycohepten-5-ylidene)-1-(3,5-dimethoxycinnamyl)piperidine, 4(5H-dibenzo[a,d]cyclohepten-5-ylidene)-1-(2-methoxycinnamyl)piperidine, 4-(5H-dibenzo[a,d]cyclohepten-5-ylidene)-1-(3-methoxycinnamyl)-piperidine, 4-(5H-dibenzo[a,d]cyclohepten-5-ylidene)-1-(4-methoxycinnamyl)-piperidine, 4-(10,11-dihydro-5H-dibenzo[a,d]cyclohepten-5-ylidene)-1(4-nitrocinnamyl)piperidine, 1-(4-aminocinnamyl)-4-(10,11-dihydro-5H-dibenzo[a,d]cyclohepten-5-ylidene)piperidine, 1-(4-acetylaminocinnamyl)-4-(10,11-dihydro-5H-dibenzo[a,d]cyclohepten-5-ylidene)piperidine, 4-(5H-dibenzo[a,d]cyclohepten-4-ylidene)-1-(4-fluorocinnamyl)piperidine, 4-(5H-dibenzo[a,d]cyclohepten-5-ylidene)-1-(4-hydroxycinnamyl)piperidine, 1-(4-acetoxycinnamyl)-4-(5H-dibenzo[a,d]cyclohepten-5-ylidene)piperidine, 4(5H-dibenzo[a,d]cyclohepten-5-ylidene)-1(4-hydroxy-3-methoxycinnamyl)-piperidine, 1-(4-acetoxy-3-methoxycinnamyl)-4-(5H-dibenzo[a,d]cyclohepten-5-ylidene)piperidine, 4-(5H-dibenzo[a,d]cyclohepten-5-ylidene)-1-(3-hydroxycinnamyl)piperidine, 1-(3-acetoxycinnamyl)-4-(5H-dibenzo[a,d]cyclohepten-5-ylidene)-piperidine, 4-(5H-dibenzo[a,d]cyclohepten-5-ylidene)-1-[3-(2-methoxyacetoxy)cinnamyl]piperidine, 4-(5H-dibenzo[a,d]cyclohepten-5-ylidene)-1-(2-methoxycarbonylcinnamyl)piperidine, 4-(5H-dibenzo[a,d]cyclohepten-5-ylidene)-1-(4-methoxycarbonylcinnamyl)piperidine, 4-(5H-dibenzo[a,d]cyclohepten-5-ylidene)-1-(3-methoxy-2-nitrocinnamyl)piperidine, 4-(5H-dibenzo[a,d]cyclohepten-5-ylidene)-1-(4-ethoxycarboxycinnamyl)piperidine, 4-(5H-dibenzo[a,d]cyclohepten-5-ylidene)-1-(4-methoxyacetoxycinnamyl)piperidine, 4-(5H-dibenzo[a,d]cyclohepten-5-ylidene)-1-(3,4-dihydroxycinnamyl)piperidine, 4-(10,11-dihydro-5-H-dibenzo[a,d]cyclohepten-5-ylidene)-1-(2,4-aminosulfonylcinnayml)-4-(10,11-dihydro-5H-dibenzo[a,d]cyclohepten-5-ylidene)piperidine, 1-(4-aminosulfonyl-α-methylcinnamyl)-4-(5H-dibenzo[a,d]cyclohepten-5-ylidene)piperidine, 1-(4-aminosulfonyl-β-methylcinnamyl)-4-(5H-dibenzo[a,d]cyclohepten-5-ylidene)piperidine, 1-(2-chlorobenzyl)-4-(5H-dibenzo[a,d]cyclohepten-5-ylidene)piperidine, 1-cyclohexyl-3-[4-(5H-dibenzo[a,d]cyclohepten-5-ylidene)-1-piperidinyl]propane, 1-cyclohexyl-4-[4-(5H-dibenzo[a,d]cyclohepten-5-ylidene)-1-piperidinyl]butane, 4-(5H-dibenzo[a,d]cyclohepten-5-ylidene)-1-hexylpiperidine, 1-decyl-4-(5H-dibenzo[a,d]cyclohepten-5-ylidene)piperidine, 5-[4-(5H-dibenzo[a,d]cyclohepten-5-ylidene)-1-piperidinyl]-2-(3,4-dichlorophenyl-2-isopropylvaleronitrile, 4-(5H-dibenzo[a,d]cyclohepten-5-ylidene)-1-[3-[2-(cinnamoylamino)phenylthio]-1-propyl)piperidine, 4-(5H-dibenzo[a,d]cyclohepten-5-ylidene)-1-cinnamylpiperidine, 5-[4-(5H-dibenzo[a,d]cyclohepten-5-ylidene)-1-piperidinyl]-2,2-diphenylvaleronitrile, 5-[4-(5H-dibenzo[a,d]cyclohepten-5-ylidene)-1-piperidinyl]-2-(3-trifluoromethylphenyl)-2-isopropylvaleronitrile, 4-(5H-dibenzo[a,d]cyclohepten-5-ylidene)-1-(2-fluorobenzyl)piperidine, 4-(5H-dibenzo[a,d]cyclohepten-5-ylidene)-1-(4-fluorophenylethyl)piperidine, 5-[4-(5H-dibenzo[a,d]cyclohepten-5-ylidene)-1-piperidinyl]-2-(3-trifluoromethylphenyl)valeronitrile, 1-(3-aminobenzyl)-4-(5H-dibenzo[a,d]cyclohepten-5-ylidene)-piperidine, 4-[4-(5H-dibenzo[a,d]cyclohepten-5-ylidene)-1-piperidinyl]-3',4'-dimethoxybutyrophenone, 1-(4-cyanobenzyl)-4-(5H-dibenzo[a,d]cyclohepten-5-ylidene)-1-piperidine, 1-cyclohexyl-4-[4-(10,11-dihydro-5H-dibenzo[a,d]cyclohepten-5-ylidene)-1-piperidinyl]butane, cyclohexyl-[4-(5H-dibenzo[a,d]cyclohepten-5-ylidene)-1-piperidinyl]methane, 4(5H-dibenzo[a,d]cyclohepten-5-ylidene)-1-(2,3-dimethoxybenzyl)piperidine, 3-cyanopropyl-4-(5H-dibenzo[a,d]cyclohepten-5-ylidene)piperidine, 4-(5H-dibenzo[a,d]cyclohepten-5-ylidene)-1-(3,4-dimethoxyphenacyl)piperidine, 1-cyclohexyl-6-[4-(5H-dibenzo[a,d]cyclohepten-5-ylidene)-1-piperidinyl]hexane.

3. A method according to claim 1, in which the administration is an oral administration of a daily dose of from 0.001 to 2000 mg of the piperidine derivative or pharmaceutically acceptable salt thereof.

4. A method according to claim 1, in which the administration is a parenteral administration of a daily dose of from 0.001 to 1000 mg of the piperidine derivative or pharmaceutically acceptable salt thereof.

5. A method according to claim 1, in which the administration is of a unit dose of from 0.001 to 500 mg of the piperidine derivative or pharmaceutically acceptable salt thereof.

* * * * *